United States Patent
Donahue

(10) Patent No.: US 12,207,932 B2
(45) Date of Patent: Jan. 28, 2025

(54) VENTRICULAR ARRHYTHMIAS AND RELATED METHODS

(71) Applicant: University of Massachusetts, Boston, MA (US)

(72) Inventor: John Kevin Donahue, Hopkinton, MA (US)

(73) Assignee: University of Massachusetts, Westborough, MA (US)

( * ) Notice: Subject to any disclaimer, the term of this patent is extended or adjusted under 35 U.S.C. 154(b) by 575 days.

(21) Appl. No.: 17/600,271

(22) PCT Filed: Apr. 2, 2020

(86) PCT No.: PCT/US2020/026362
§ 371 (c)(1),
(2) Date: Sep. 30, 2021

(87) PCT Pub. No.: WO2020/206103
PCT Pub. Date: Oct. 8, 2020

(65) Prior Publication Data
US 2022/0167907 A1 Jun. 2, 2022

Related U.S. Application Data

(60) Provisional application No. 62/829,233, filed on Apr. 4, 2019.

(51) Int. Cl.
*A61B 5/363* (2021.01)
*A61B 5/367* (2021.01)
*C12N 15/113* (2010.01)
*C12N 15/86* (2006.01)

(52) U.S. Cl.
CPC .............. *A61B 5/363* (2021.01); *A61B 5/367* (2021.01); *C12N 15/113* (2013.01); *C12N 15/86* (2013.01); *C12N 2310/11* (2013.01); *C12N 2320/33* (2013.01)

(58) Field of Classification Search
CPC ............ A61B 5/363; A61B 5/367; A61B 5/36
See application file for complete search history.

(56) References Cited

U.S. PATENT DOCUMENTS

| 7,016,719 B2 | 3/2006 | Rudy et al. |
| 2014/0073687 A1 | 3/2014 | Chien et al. |
| 2015/0183842 A1 | 7/2015 | Donahue et al. |

(Continued)

OTHER PUBLICATIONS

International Search Report and Written Opinion for Application No. PCT/US2020/026362 mailed Jul. 22, 2020.

(Continued)

*Primary Examiner* — George R Evanisko
(74) *Attorney, Agent, or Firm* — Sunstein LLP

(57) ABSTRACT

In some aspects, the disclosure relates methods for identifying ventricular tachycardia in subjects, e.g., subjects who have previously experienced a myocardial infarction. In some embodiments, methods of the disclosure comprise measuring action potential durations and/or expression levels of KCNE3 and/or KCNE4 in a subject. In some aspects, the disclosure relates to methods and compositions for reducing or inhibiting the activity of KCNE3 and/or KCNE4, for example, in subjects having ventricular tachycardia.

8 Claims, 13 Drawing Sheets

Specification includes a Sequence Listing.

(56) References Cited

U.S. PATENT DOCUMENTS

| | | |
|---|---|---|
| 2017/0367603 A1 | 12/2017 | Spector |
| 2019/0008584 A1* | 1/2019 | Chinyere ............... A61B 5/287 |

OTHER PUBLICATIONS

International Preliminary Report on Patentability for Application No. PCT/2020/026362 mailed Oct. 14, 2021.

Abbott et al., Kcne4 Deletion Sex-Dependently Alters Vascular Reactivity. J Vasc Res. 2016;53(3-4):138-148. doi: 10.1159/000449060. Epub Oct. 7, 2016.

Barro-Soria et al., KCNE1 and KCNE3 modulate KCNQ1 channels by affecting different gating transitions. Proc Natl Acad Sci U S A. Aug. 29, 2017;114(35):E7367-E7376. doi: 10.1073/pnas.1710335114. Epub Aug. 14, 2017.

Calkins et al., Catheter ablation of ventricular tachycardia in patients with structural heart disease using cooled radiofrequency energy: results of a prospective multicenter study. Cooled RF Multi Center Investigators Group. J Am Coll Cardiol. Jun. 2000;35(7):1905-14. doi: 10.1016/s0735-1097(00)00615-x.

De Bakker et al., Reentry as a cause of ventricular tachycardia in patients with chronic ischemic heart disease: electrophysiologic and anatomic correlation. Circulation. Mar. 1988;77(3):589-606. doi: 10.1161/01.cir.77.3.589.

De Chillou et al., Isthmus characteristics of reentrant ventricular tachycardia after myocardial infarction. Circulation. Feb. 12, 2002;105(6):726-31. doi: 10.1161/hc0602.103675.

Dun et al., Diverse phenotypes of outward currents in cells that have survived in the 5-day-infarcted heart. Am J Physiol Heart Circ Physiol. Aug. 2005;289(2):H667-73. doi: 10.1152/ajpheart.00180.2005. Epub Apr. 8, 2005.

Hegyi et al., Complex electrophysiological remodeling in postinfarction ischemic heart failure. Proc Natl Acad Sci U S A. Mar. 27, 2018;115(13):E3036-E3044. doi: 10.1073/pnas.1718211115. Epub Mar. 12, 2018.

Horácek et al., Noninvasive electrocardiogramaging of chronic myocardial infarct scar. J Electrocardiol. Nov.-Dec. 2015;48(6):952-8. doi: 10.1016/j.jelectrocard.2015.08.035. Epub Aug. 28, 2015.

Jiang et al., Delayed rectifier K currents have reduced amplitudes and altered kinetics in myocytes from infarcted canine ventricle. Cardiovasc Res. Oct. 2000;48(1):34-43. doi: 10.1016/s0008-6363(00)00159-0.

Kelemen et al., Heterogeneous repolarization creates ventricular tachycardia circuits in healed myocardial infarction scar. Nat Commun. Feb. 11, 2022;13(1):830. doi: 10.1038/s41467-022-28418-1.

Sasano et al., Molecular ablation of ventricular tachycardia after myocardial infarction. Nat Med. Nov. 2006;12(11):1256-8. doi: 10.1038/nm1503. Epub Oct. 29, 2006.

Sasano et al., Ventricular tachycardia from the healed myocardial infarction scar: validation of an animal model and utility of gene therapy. Heart Rhythm. Aug. 2009;6(8 Suppl):S91-7. doi: 10.1016/j.hrthm.2009.03.048. Epub Apr. 1, 2009.

Zhang et al., The Electrophysiological Substrate of Early Repolarization Syndrome: Noninvasive Mapping in Patients. JACC Clin Electrophysiol. Aug. 2017;3(8):894-904. doi: 10.1016/j.jacep.2016.12.017. Author Manuscript. 20 pages.

Zimmermann et al., Analysis of region specific gene expression patterns in the heart and systemic responses after experimental myocardial ischemia. Oncotarget. May 17, 2017;8(37):60809-60825. doi: 10.18632/oncotarget.17955.

\* cited by examiner

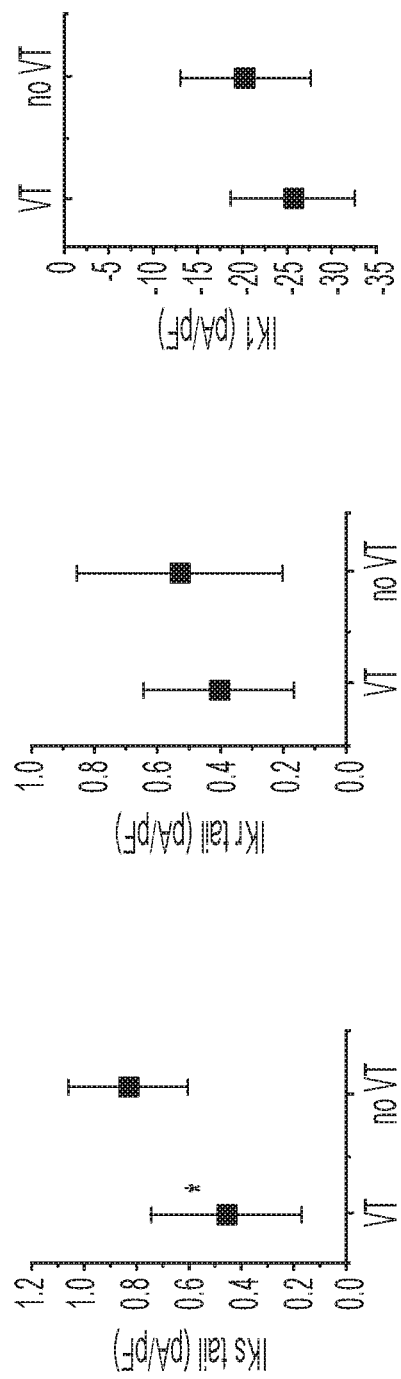
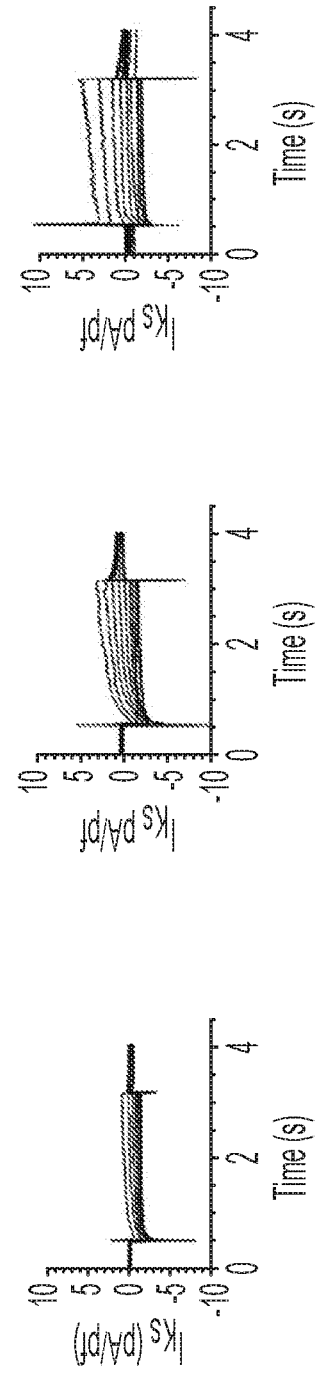
FIG. 5B
FIG. 5C

VENTRICULAR ARRHYTHMIAS AND RELATED METHODS

RELATED APPLICATION

This application is a national stage filing under 35 U.S.C. § 371 of international PCT application PCT/US2020/026362, filed Apr. 2, 2020, which claims priority under 35 U.S.C. § 119(e) to U.S. provisional patent application, U.S. Ser. No. 62/829,233, filed Apr. 4, 2019, the entire contents of each of which are incorporated herein by reference.

GOVERNMENT SUPPORT

This invention was made with government support under grant numbers HL067148 and HL134185, awarded by the National Institutes of Health. The government has certain rights in the invention.

BACKGROUND

Cardiac arrest is a leading cause of death in the developed world. Half of cardiac arrest victims have evidence of prior myocardial infarction. The healed infarct scar contains a substrate that supports reentrant ventricular arrhythmias, and death is frequently caused by ventricular tachycardia (VT) originating in the infarct scar border. The underlying cellular and tissue electrophysiology that allow reentrant VT to exist in the infarct border zone is poorly understood.

SUMMARY

Aspects of the disclosure relate to compositions and methods for diagnosing and/or treating ventricular tachycardia (VT) in a subject. The disclosure is based, in part, on identification of certain genes (e.g., genes encoding ion channel subunits, such as KCNE3, KCNE4, etc.) which are upregulated in cardiac tissue (e.g., tracts of myocardial cells residing in an infarct scar). In some embodiments, upregulation of these genes results in repolarization heterogeneity of the cardiac tissue, thereby creating a tissue substrate that can allow the initiation and/or maintenance of VT.

Accordingly, in some aspects, the disclosure provides a method for identifying ventricular tachycardia (VT) circuits in the heart of a subject. In some embodiments, the method for identifying VT circuits in the heart of a subject comprises measuring a first action potential duration (APD) of a first tract of myocardial tissue of a subject; measuring a second action potential duration (APD) of a second tract of myocardial tissue that is adjacent to the first tract; comparing the length of the first APD to the second APD; and identifying a VT circuit in the heart of the subject when the first APD is different from the second APD.

Some aspects of the disclosure provide an assay method comprising measuring a first action potential duration (APD) of a first tract of myocardial tissue of a patient who is at risk for having a ventricular tachycardia (VT) circuit; measuring a second action potential duration (APD) of a second tract of myocardial tissue that is adjacent to the first tract; comparing the length of the first APD to the second APD; and identifying a VT circuit in the heart of the patient when the first APD is different from the second APD.

In some embodiments, the measured APDs are used to generate a map of the endocardial, mid-myocardial and/or epicardial surfaces of the heart. In some embodiments, the measured APDs are used to generate a map of the APD heterogeneities and to identify VT circuits in or between the endocardial, mid-myocardial and/or epicardial surfaces of the heart.

In some embodiments, the subject or patient has had at least one myocardial infarction. In some embodiments, the subject has or is suspected of having a heart defect or disease.

In some embodiments, the first tract and/or the second tract are located within a myocardial infarct scar of the heart. In some embodiments, the first tract is located partially or completely within a myocardial infarct scar of the heart. In some embodiments, the second tract is located partially or completely within a myocardial infarct scar of the heart. In some embodiments, the first APD and/or the second APD are measured in vivo by unipolar or bipolar electrogram, or monophasic action potential (MAP) recording. In some embodiments, the first APD and/or the second APD are measured by optical mapping. Measuring may comprise non-invasive electrocardiographic imaging or non-invasive recording of cardiac electrical activity, for example by non-invasive mapping of unipolar activation-recovery intervals during sinus rhythm or fixed rate pacing of the subject's heart. In some embodiments, the recording comprises endocardial or epicardial mapping of sinus rhythm unipolar electrograms of the subject.

The first tract and/or second tract may be characterized by up-regulation of KCNE3 or KCNE4 relative to heart tissue outside of the first or second tract. In some embodiments, if the first tract is characterized by up-regulation of KCNE3, the second tract is characterized by upregulation of KCNE4. In some embodiments, if the first tract is characterized by up-regulation of KCNE4, the second tract is characterized by upregulation of KCNE3.

In some embodiments, a method for identifying ventricular tachycardia (VT) circuits further comprises the step of administering a composition (e.g., an inhibitory nucleic acid) that inhibits expression of KCNE3, a composition that inhibits expression of KCNE4, or a combination thereof. In some embodiments, an inhibitory nucleic acid is an antisense oligonucleotide (ASO), dsRNA, siRNA, shRNA, miRNA, or artificial miRNA (ami-RNA). In some embodiments, an siRNA comprises any one of the sequences as provided in Table 1. In some embodiments, an isolated nucleic acid encodes a dominant-negative variant of KCNE3 protein, optionally wherein the dominant-negative variant is KCNE3-V68T or KCNE3-V72T. In some embodiments, an isolated nucleic acid encodes a dominant-negative variant of KCNE4 protein. In some embodiments, an isolated nucleic acid is comprised in a recombinant adeno-associated virus (rAAV).

In some embodiments, a method for identifying ventricular tachycardia (VT) circuits comprises the step of ablating the cells of the VT circuit, for example by laser ablation or catheter-based ablation. In some embodiments, a method for identifying ventricular tachycardia (VT) circuits enables the identification of subjects, e.g., patients, at risk for having VT circuits and/or who would benefit from preventative or curative therapies, e.g., ablation or implantable defibrillators.

In some aspects, the disclosure provides a method for treating a subject having a cardiac ventricular tachycardia (VT) circuit, the method comprising administering a composition to a subject, wherein the composition inhibits expression of KCNE3, KCNE4, or a combination thereof. A composition may comprise an inhibitory nucleic acid (e.g., a hairpin-forming RNA, a short interfering RNA (siRNA), or an antisense oligonucleotide (ASO)) that targets a KCNE3 and/or KCNE4 gene. In some embodiments, the subject has been determined to have a myocardial infarct scar characterized by a ventricular tachycardia (VT) circuit.

In some embodiments, the step of determining comprises measuring a level of KCNE3 in a first location of the myocardial infarct scar that is elevated relative to the level of KCNE3 at a location of the subject's heart outside of the myocardial infarct scar. In some embodiments, the elevated level at the first location is at least 1.5 times greater than the location outside of the scar.

In some embodiments, the determining comprises measuring a level of KCNE4 in a second location of the myocardial infarct scar that is elevated relative to the level of KCNE4 at a location of the subject's heart outside of the myocardial infarct scar. In some embodiments, the elevated level is at least 4 times greater than the location outside of the scar. In some embodiments, the first location and the second location of the myocardial infarct scar do not comprise the same cells. In some embodiments, the determining comprises identifying heterogeneous action potential durations (APDs) within a myocardial infarct scar of the subject, wherein the identifying comprises measurement of APDs by in vivo unipolar or bipolar electrogram, monophasic action potential (MAP) recording, or optical mapping.

In some embodiments, a method for treating a subject having a cardiac ventricular tachycardia (VT) circuit comprises the step of ablating the cells of the VT circuit (e.g., located on epicardial tissue or endocardial tissue), for example by laser ablation or catheter-based ablation.

In some embodiments, a composition comprises a nucleic acid that encodes a dominant-negative variant of KCNE3 protein, optionally a KCNE3 protein comprising a V68T or V72T mutation. In some embodiments, a dominant-negative variant of KCNE3 protein comprises the amino acid sequence set forth in SEQ ID NO: 29 or 31. In some embodiments, the dominant-negative variant of KCNE3 protein is encoded by the nucleic acid sequence set forth in SEQ ID NO: 30 or 32. In some embodiments, a composition comprises a nucleic acid that encodes a dominant-negative variant of KCNE4 protein.

In some aspects, the disclosure provides an isolated nucleic acid comprising a transgene having a nucleic acid that encodes a dominant-negative variant of KCNE3 protein. In some embodiments, the transgene is flanked by adeno-associated virus (AAV) inverted terminal repeats (ITRs). In some embodiments, the dominant-negative variant of KCNE3 protein comprises a V68T mutation. In some embodiments, the dominant-negative variant of KCNE3 protein comprises the amino acid sequence set forth in SEQ ID NO: 29. In some embodiments, the dominant-negative variant of KCNE3 protein is encoded by the nucleic acid sequence set forth in SEQ ID NO: 30. In some embodiments, the dominant-negative variant of KCNE3 protein comprises a V72T mutation. In some embodiments, the dominant-negative variant of KCNE3 comprises the amino acid sequence set forth in SEQ ID NO: 31. In some embodiments, the dominant-negative variant of KCNE3 protein is encoded by the nucleic acid sequence set forth in SEQ ID NO: 32. In some embodiments, the transgene comprises a promoter (e.g., a constitutive promoter, an inducible promoter, or a tissue-specific promoter) that is operably linked to the nucleic acid encoding the dominant-negative variant of KCNE3 protein. In some embodiments, the promoter is a heart tissue-specific promoter, for example an α-cardiac actin promoter, a cardiac Troponin T (cTnT) promoter, a cardiac Troponin C promoter (cTnC), or a sodium-calcium exchanger promoter (NCX). In some embodiments, the isolated nucleic acid is located in a vector. In some embodiments, the vector is a plasmid or a viral vector.

In some aspects, the disclosure provides a recombinant adeno-associated virus (rAAV) comprising (i) an isolated nucleic acid comprising a transgene having a nucleic acid that encodes a dominant-negative variant of KCNE3 protein; and (ii) an AAV capsid protein (e.g., a capsid protein having a tropism for cardiac tissue). In some embodiments, the transgene is flanked by adeno-associated virus (AAV) inverted terminal repeats (ITRs).

BRIEF DESCRIPTION OF DRAWINGS

FIG. 2A shows that expression levels of KCNE3, KCNE3 and KCNJ2 were statistically different in the VT site compared to both no-VT and uninfarcted sites, signifying a unique change within the VT circuit. FIG. 2B shows that expression levels of GJA1, CACNA1C, and KCNQ1 were decreased at both VT sites compared to uninfarcted myocardium but were not different between the two border zone sites. FIG. 2C shows that expression levels of KCNH2, KCNE1, KCNE2 and SCN5A were not statistically different between the 3 tested sites. $*p<0.05$ vs. no-VT and noninfarcted, $\dag p<0.05$ vs. noninfarcted, $\ddag p<0.01$ vs. noninfarcted, $\#p<0.05$ vs no-VT and $p<0.01$ vs noninfarcted.

FIG. 3A shows action potential durations (APD) at the indicated sites in the left panel for a single VT animal. The grayed region is the infarct scar; the dashed circle is the mapped VT circuit location. The right panel shows the response to abrupt shortening of the pacing cycle length. Transient conduction block occurs at the VT site and all of the surrounding sites continue to conduct the paced stimulus. FIG. 3B shows action potential durations (APD) in a no-VT animal with more homogeneous action potential durations and uniform conduction with the shift from longer to shorter pacing cycle length. FIG. 3C provides summary data comparing APD and bipolar electrogram width. The analysis from the VT animals included the mapped VT site and 3 adjacent sites (square) and 4 adjacent sites on the opposite side of the infarct scar from the VT site (triangle). In the no-VT animals (circle), 4 adjacent electrograms from a site anatomically matched to the VT site in the VT animals were used. The primary cohort of animals is depicted with the solid symbol, and the validation cohort of VT animals is depicted with the vertical-lined symbol. ‡ p<0.001 comparing VT site to opposite site in VT animals and to anatomically matched site in no-VT animals.

FIG. 4A is an isochronal map of a VT circuit. Continuous activation of the entire VT cycle length was observed along a single surface of the tissue wedge. The filled circles show the locations on the activation map where example pixels shown at the right were located. The empty central region had 2:1 activation and did not participate in the VT. FIG. 4B is a map showing action potential duration (APD) during pacing at a cycle length of 1000 ms for the VT circuit tissue shown in FIG. 4A. The colored boxes show the locations on the APD map for the example electrograms at the right side of the figure. The VT circuit consisted of tissues with relatively short APDs in contact with tissues that had relatively long APDs. FIG. 4C is an APD map from a tissue wedge that had inducible VT but that did not have the complete circuit. FIG. 4D is an APD map from a no-VT animal. FIG. 4E provides summary data illustrating that all infarct wedges in all animals show that the range and standard deviation of APD measurements across the mapping field was significantly increased in the VT circuit wedges. No significant differences were noted for mean APD or for either mean or standard deviation of conduction velocity (CV) measures. ‡ p<0.001 VT site vs. all other groups, * p=0.01 VT wedges without full circuit vs. no-VT animal and p=0.08 vs. uninducible wedges from VT animals, ** p=0.03 VT wedges without full circuit vs. no-VT animal and p=0.13 vs. uninducible wedges from VT animals.

FIGS. 5A-5C demonstrate a patch clamp analysis of action potentials and potassium currents from cells harvested at mapped VT sites in VT animals compared to anatomically matched sites in no-VT animals. FIG. 5A show that action potential duration measurements taken during current clamp mode show greater variability in APD for the VT site but no difference in average APD (similar to the in vivo measurements of APD in FIG. 3). No differences were noted in resting membrane potential (RMP) or maximum rate of rise of the action potential (dV/dtmax); both were reduced relative to reported values for normal animals. The right panel shows all of the APDs recorded for a single VT animal compared to a single no-VT animal. FIG. 5B shows the average potassium currents obtained during voltage clamp mode are shown for the 3 prominent cardiac ventricular repolarizing currents. Average potassium channel (IKs) was significantly reduced at the VT sites. * p=0.03 FIG. 5C shows that the average current measurement did not adequately describe the complexity of changes in IKs. Variability of IKs measured from different cells taken within the VT region from a single animal is shown.

FIG. 6A illustrates that basic components of the circuit include surviving strands of myocardium interrupted by areas of fibrosis. A strand with shorter APD is adjacent to a strand with longer APD. Both limbs of the circuit may be entirely inside the scar as shown, or either may be outside the scar border (e.g. outer loop). The circuit connects to the rest of the heart (‡) and may connect to dead-end segments (*). FIG. 6B illustrates that VT starts with a premature beat (□) that conducts through the surviving myocardial tissue strand until it reaches the junction point between short and long APD tissues. It continues to conduct down the path with shorter APDs that has recovered excitability and it blocks in the path with longer APDs that is still refractory. When the excitation wavefront reaches the distal connection between the two limbs of the circuit, it continues to conduct back up the long APD limb if that path has recovered excitability. As the tissue continues to be activated at rapid rates, the APDs shorten as a rate related response. The excitation wavefront continues to conduct as long as tissue in front of the wavefront has recovered excitability prior to arrival of the excitation wavefront.

DETAILED DESCRIPTION

Figure 1:
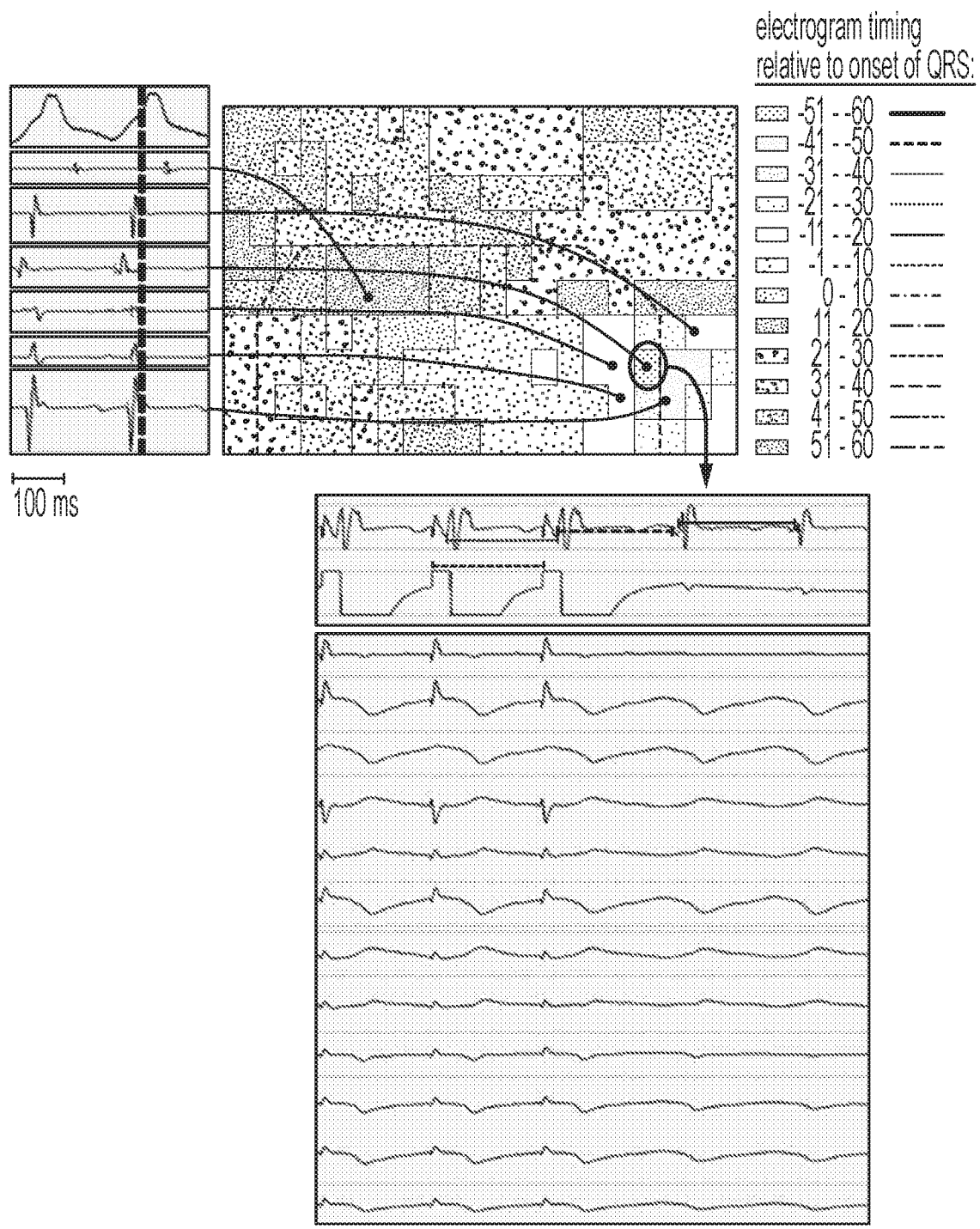
FIG. 1 shows a schematic depicting the one embodiment of ventricular tachycardia (VT) mapping, including example electrograms and a surface electrocardiogram (ECG) strip (top left panel), a graphical display of the activation time during VT for each catheter location (top right panel with markers showing the location of the example electrograms), and entrainment pacing from the site of earlies activation (local electrograms in the middle panel and 12-lead ECG in the bottom panel). The activation mapping process started by moving the catheter throughout the heart during VT, obtaining an electrogram and marking the catheter location at each site, and measuring the timing of each electrogram (top left panel, dashed lines) against a fiduciary point in the surface ECG. The activation time and location for each point was displayed graphically (top right panel). Overlaid on the activation map is the edge of the infarct scar (dotted line) obtained from a separately performed sinus rhythm voltage map of the same region. Scar border zone was conventionally defined as the area with bipolar voltage less than 1.5 mV. After the site of earliest activation was identified (circled in top right panel), the catheter was placed at that location and paced during VT at an output just above threshold and a cycle length 10 milliseconds (ms) faster than the tachycardia cycle length. Local electrograms are recorded from the pacing electrodes and the closest adjacent bipole (middle panel, pacing bottom tracing, closest adjacent top tracing). Local capture was confirmed by comparing the timing of the pacing stimulus to the adjacent electrogram.

Aspects of the disclosure relate to methods of identifying and treating ventricular tachycardia (VT) circuits in the myocardium or heart of a subject, e.g., a human subject. In some embodiments, methods include non-invasive electrocardiographic imaging (ECGi) or invasive arrhythmia mapping of myocardial tissue to determine action potential durations (APDs) resulting from monophasic action potential (MAP) recordings. Generally, MAP recordings may be taken at multiple sites or locations within the heart of the subject, e.g., across an infarct scar border, at a transmural surface of the ventricular septum, or in a wall of the endocardium. The length of an APD (e.g., the amount of time that passes between depolarization and repolarization of cells) may be uniform or heterogeneous when comparing across multiple sites. In some embodiments, assessments of the APD at different sites identify repolarization heterogeneity across the heart, (e.g., non-uniform APD lengths between two cardiac locations. The disclosure is based, in part, on the recognition that the occurrence of myocardial sites characterized by repolarization heterogeneity (e.g., a location having short APDs adjacent or proximal to a location having long APDs) is characteristic of a VT circuit.

Aspects of the disclosure relate to genes encoding certain sodium channel subunits (e.g., KCNE3, KCNE4, etc.) which are up-regulated in VT circuit myocardial cells relative to healthy myocardial cells. In some embodiments, methods of identifying VT circuits include quantification of expression levels, e.g., mRNA expression or protein expression, of KCNE3 and/or KCNE4 in cardiac tissue of a subject (e.g., measuring mRNA levels at multiple sites within the heart of the subject). In some embodiments, overexpression of KCNE3 and/or KCNE4, e.g., elevated or increased expression relative to a control site, e.g., uninfarcted myocardia, is characteristic of a VT circuit.

Some aspects of the disclosure relate to methods and compositions for modulating (e.g., decreasing) the activity of KCNE3 and/or KCNE4 in a cell or subject. In some embodiments, of the disclosure provides an isolated nucleic acid comprising an inhibitory nucleic acid that reduces the expression of KCNE3 and/or KCNE4, e.g., an shRNA or RNAi that targets KCNE3. In some embodiments, an isolated nucleic acid encodes a protein that functionally competes with KCNE3 and/or KCNE4, e.g., a KCNQ1 potassium channel alpha subunit. In some embodiments, an isolated nucleic acid that encodes a protein that functionally competes with KCNE3 or KCNE4 is a dominant-negative variant of KCNE3 or KCNE4, e.g., KCNE3-V68T or KCNE3-V72T.

Methods of Identifying VT Circuits Using APDs

The disclosure relates, in some aspects, to assessment of action potential durations (APD) on MAP recordings of a subject having or suspected of having ventricular tachycardia (VT). Ventricular tachycardia (VT) generally refers to a heart condition wherein a subject experiences an abnormally high heart rate that arises from improper electrical activity in the ventricles of the heart. In some embodiments, myocardial tissue suffering from ventricular tachycardia (VT) comprises VT circuits comprising a heterogeneous pattern of myocardial sites, with sites comprising short APDs adjacent to sites comprising long APDs. In some aspects, the disclosure relates to positive identification of VT circuits (e.g., circuits characterized by a heterogeneous pattern of myocardial sites) enables the in subjects, e.g., subjects having previously experienced a myocardial infarction, by measuring the APDs of monophasic action potential (MAP) recordings at multiple sites within the heart of a subject and comparing the relative lengths of said APDs. The presence of a myocardial site with a short APD adjacent to a myocardial site with a long APD indicates, in some embodiments, that these sites are part of, or proximal to, a VT circuit.

As used herein, the term 'action potential duration' (APD) refers to the period or length of time over which the membranes of myocardial cells, e.g., at a single site, experience a change in voltage during depolarization or repolarization. The change in voltage typically results from the movement of ions through ion channels, e.g., potassium voltage-gated channels, such as potassium voltage-gated channels comprising KCNE3 subunits and/or KCNE4 subunits. In some embodiments, heterogeneity of the lengths of APDs at multiple sites, e.g., at two or more sites or locations of a population of cells or tissue in the heart of a subject, e.g., a subject having previously experienced a myocardial infarction. In some embodiments, a VT circuit is characterized or identified by a tract of myocardial cells with short APDs adjacent to a tract of myocardial cells with long APDs. As used herein, the term "multiple sites" generally refers to.

MAP recordings to measure APDs may be performed using non-invasive electrocardiographic imaging (ECGi) or invasive arrhythmia mapping. In some embodiments, a MAP is recorded or measured under conditions that allow for the reproduction of the repolarization time course of cellular transmembrane action potentials. In some embodiments, ECGi refers to detailed three-dimensional mapping of cardiac arrhythmia in order to record heart rhythm information. In some embodiments, ECGi is performed using a CardioInsight mapping procedure. Methods of measuring ECGi are known, for example as described in U.S. Pat. No. 7,016,719.

In some embodiments, unipolar electrogram recordings to determine the activation-recovery interval may be measured in addition to, or in place of, measurement of an APD. In some embodiments, measurements of an APD may be approximated using any other measurement known to a person skilled in the art. In some embodiments, an alternative measurement of cardiac function may be used as a surrogate for measurement of an APD.

In some embodiments, MAP recordings may be obtained during fixed rate pacing, e.g., from catheter poles for 8 beats at 400 ms followed by an abrupt switch to 250 ms for an additional 8 beats. In some embodiments, at each MAP site, unipolar or bipolar electrograms may be recorded during sinus rhythm. Invasive arrhythmia mapping generally refers to detailed three-dimensional mapping of cardiac arrhythmia that requires a subject to undergo an invasive heart catheterization procedure under light sedation prior to recording heart rhythm information. In some embodiments, invasive arrhythmia mapping is performed using a Carto, Rythmia or Ensite-NavX mapping procedure.

MAP recordings to measure APDs may be measured at multiple sites. In some embodiments, multiple sites, e.g., in the heart of a subject, comprise two or more myocardial tissue tracts. In some embodiments, a VT circuit is characterized by myocardial sites with short APDs adjacent to myocardial sites with long APDs. In some embodiments, two or more sites are "adjacent" to each another, meaning that they are located within the same area of the heart as one another, e.g., located in the endocardium of the right ventricle. In some embodiments, two or more sites are adjacent to each another if they comprise a population of cells, tissue, or tissue tracts that are millimeters, e.g., 1-5, 2-10, or 5-20 mm, apart. In some embodiments, MAP recordings are measured at a minimum of 10, 15, 20, 25, 30, 35, 40, 45, 50, 55, 60, 65, 70, 75, 80, 85, 90, 95, or 100 or more unique sites in a subject. In some embodiments, each site comprises a population of cells or tissue tract, wherein each population of cells or tissue tract may be in the area within an infarct scar or near an infarct scar, e.g., within the border zone of an infarct scar. In some embodiments, a site, e.g., a population of cells or tissue tract, is contacting or touching another site, e.g., a population of cells or tissue tract. In some embodiments, two or more sites are adjacent to each another if they comprise a population of cells, tissue, or tissue tracts that are 1-100, 1-50, 2-10, 5-50, 10-50, 25-100, 50-100, 50-200, 100-200, 100-400, 250-400, 300-400, 300-500, 400-500, 450-550, 500-600, 550-650, 600-700, 650-750, 700-800, 750-850, 800-900, 850-950, or 900-1000 nm apart. In some embodiments, two or more sites are adjacent to each another if they comprise a population of cells, tissue, or tissue tracts that are 1-10, 1-5, 2-10, 3-10, 5-10, 7-10, 10-15, 15-20, 20-25, 25-30, 30-40, 40-50, 50-60, 60-70, 70-80, 80-90, 90-100, or 25-50 mm apart.

In some embodiments, an APD at a site belonging to a VT circuit has an average or mean length of approximately 230 milliseconds (ms). In some embodiments, an APD at a site belonging to a VT circuit has an average length of approximately 200-250, 200-210, 210-220, 220-230, 230-240, or 240-250 ms. In some embodiments, the standard deviation of the length of an APD at a site belonging to a VT circuit is approximately 35 ms. In some embodiments, the standard deviation of the length of an APD at a site belonging to a VT circuit is approximately 25-50, 25-30, 30-35, 35-40, 40-45, or 45-50 ms. In some embodiments, the range of the length of an APD at a site belonging to a VT circuit is approximately 80 ms. In some embodiments, the range of the length of an APD at a site belonging to a VT circuit is approximately 50-110, 50-60, 60-70, 80-90, 90-100, or 100-110 ms.

In some embodiments, an APD at a site that is remote or distal to a VT circuit, e.g., a non-VT myocardial site that belongs to a subject having a VT circuit, has an average or mean length of approximately 230 milliseconds (ms). In some embodiments, an APD at a site that is remote or distal to a VT circuit has an average length of approximately 190-270, 190-200, 200-210, 210-220 220-230, 230-240, 240-250, 250-260, or 260-270 ms. In some embodiments, the standard deviation of the length of an APD at a site that is remote or distal to a VT circuit is approximately 20 ms. In some embodiments, the standard deviation of the length of an APD at a site that is remote or distal to a VT circuit is approximately 5-25, 5-10, 10-15, 15-20, or 20-25 ms. In some embodiments, the range of the length of an APD at a site that is remote or distal to a VT circuit is approximately 35 ms. In some embodiments, the range of the length of an APD at a site that is remote or distal to a VT circuit is approximately 20-60, 20-30, 30-40, 40-50, or 50-60 ms.

In some embodiments, an APD at a site that belongs to a subject not having a VT circuit, has an average or mean length of approximately 240 milliseconds (ms). In some embodiments, an APD at a site that belongs to a subject not having a VT circuit has an average length of approximately 200-290, 200-210, 210-220 220-230, 230-240, 240-250, 250-260, 260-270, 280-280, or 280-290 ms. In some embodiments, the standard deviation of the length of an APD at a site that belongs to a subject not having a VT circuit is approximately 20 ms. In some embodiments, the standard deviation of the length of an APD at a site that belongs to a subject not having a VT circuit is approximately 5-25, 5-10, 10-15, 15-20, or 20-25 ms. In some embodiments, the range of the length of an APD at a site that belongs to a subject not having a VT circuit is approximately 35 ms. In some embodiments, the range of the length of an APD at a site that belongs to a subject not having a VT circuit is approximately 20-50, 20-30, 30-40, or 40-50 ms.

In some embodiments, the difference between a short APD and a long APD at a site that belongs to a subject having a VT circuit may be about 50-100, about 50-60, about 60-70, about 75, about 70-80, about 80-90, or about 90-100 ms. In some embodiments, the difference between a short APD and a long APD at a site that belongs to a subject having a VT circuit may be about 50, about 60, about 70, about 75, about 80, about 90, or about 100 ms.

In some embodiments, the difference between a short APD and a long APD at a site that belongs to a subject having a VT circuit when measured by optical mapping may be about 200-300, about 200-210, about 210-220, about 220-230, about 230-240, about 240-250, about 250-260, about 260-270, about 270-280, about 280-290, or about 290-300 ms. In some embodiments, the difference between a short APD and a long APD at a site that belongs to a subject having a VT circuit when measured by optical mapping may be about 200, about 210, about 220, about 230, about 240, about 250, about 260, about 268, about 270, about 280, about 290, or about 300 ms.

Accordingly, aspects of the disclosure involve methods of identifying ventricular tachycardia (VT) circuits in the heart of a subject, comprising measuring the action potential duration (APD) of monophasic action potential (MAP) recordings, e.g., non-invasive electrocardiographic imaging (ECGi) or invasive arrhythmia mapping, at multiple sites within the heart of the subject, e.g., within and/or proximal to infarcted scar tissue resulting from a myocardial infarction; and comparing the relative lengths of the APDs at the multiple sites within the heart of the subject, e.g., comparing the average, standard deviation, and ranges of APD across multiple sites; wherein VT circuits in the heart of the subject are identified by a pattern of sites within the heart comprising short APDs adjacent to sites within the heart comprising long APDs.

In some embodiments, methods of identifying ventricular tachycardia (VT) circuits in the heart of a subject involve measuring APDs within a scar, e.g., a myocardial infarct scar, or the whole surface area of the ventricles with one or more catheters to measure multiple APDs. In some embodiments, scanning enables the identification of heterogeneities or areas with heterogeneity within the scar or surface area of the ventricles. These heterogeneities or areas with heterogeneity can then be used to create a map of these heterogeneities for therapeutic purposes, e.g., to perform a therapeutic intervention such as ablation or injection of a drug, e.g., a small molecule drug or a biological drug. In some embodiments, non-invasive imaging is used to create a similar map of heterogeneities or areas with heterogeneity within the scar or surface area of the ventricles, e.g., for therapeutic intervention or to screen patients to identify those at risk for VT. Patients identified as being at risk for VT could receive implantable defibrillators or other preventative or therapeutic measures.

KCNE3 and KCNE4

KCNE3 and KCNE4 are potassium voltage-gated transmembrane proteins that assemble with one or more types of Kv channel α subunit, e.g., the KCNQ1 Kv α subunit, to modulate, e.g., increase or decrease, the gating kinetics of the Kv channel α subunits. The KCNQ family of voltage-dependent potassium channels, e.g., KCNQ1, comprise six transmembrane domains and a characteristic pore region. KCNQ1 functionally interacts with KCNE proteins, small β-subunit protein with single transmembrane domains, to generate voltage current in myocardial sites. It was known in the art that inactivating mutations in either the KCNQ or KCNE subunits can result in the prolongation of action potentials and an increased risk of ventricular arrhythmias in patients with long QT-syndrome (LQTS). Specifically, assembly of KCNE3 with KCNQ1 forms a complete potassium voltage gated channel voltage-dependent delayed that remains constitutively open with a nearly linear relationship between current/voltage (I/V). KCNE4, when bound to calmodulin, was known in the art to strongly inhibit the KCNQ1 potassium channel.

As used herein, KCNE3, also known as "potassium voltage-gated channel subfamily E regulatory subunit 3", HYPP, HOKPP, MiRP2, or BRGDA6, generally refers to any protein or nucleic acid sequence encoded by a KCNE3 gene. In some embodiments, a KCNE3 may be of human (NCBI Gene ID 10008), pig (e.g., NCBI Gene ID 397168), non-human primate (e.g., NCBI Gene ID 718902), or rodent (e.g., NCBI Gene ID 57442) origin. In some embodiments, a KCNE3 protein comprises an amino acid sequence that is 99% identical, 95% identical, 90% identical, 80% identical, 70% identical, 60% identical, or 50% identical to the amino acid sequence set forth in GenBank RefSeq Accession Numbers XP_016872541.1, XP_016872540.1, and XP_016872537.1.

```
Amino acid sequence of wild-type KCNE3
(NCBI Reference Sequence: XP_016872541.1)
                                    (SEQ ID NO: 23)
METTNGTETWYESLHAVLKALNATLHSNLLCRPGPGLGPDN

QTEERRASLPGRDDNSYMYILFVMFLFAVTVGSLILGYTRS

RKVDKRSDPYHVYIKNRVSMI
```

As used herein, KCNE4, also known as "potassium voltage-gated channel subfamily E regulatory subunit 4", or MiRP3, generally refers to any protein or nucleic acid sequence encoded by a KCNE4 gene. In some embodiments, a KCNE4 may be of human (NCBI Gene ID 23704), pig (e.g., NCBI Gene ID 397167), non-human primate (e.g., NCBI Gene ID 723519), or rodent (e.g., NCBI Gene ID 57814) origin. In some embodiments, a KCNE3 protein comprises an amino acid sequence that is 99% identical, 95% identical, 90% identical, 80% identical, 70% identical, 60% identical, or 50% identical to the amino acid sequence set forth in GenBank RefSeq Accession Number NP_542402.3.

```
Amino acid sequence of wild-type KCNE4
(NCBI Reference Sequence: NP_542402.3)
                                (SEQ ID NO: 24)
MHFLTIYPNCSSGVVRAQSRTEQKNPLGLDDLGIQNLGQT

VSLAPAVEAASMLKMEPLNSTHPGTAASSSPLESRAAGGG

SGNGNEYFYILVVMSFYGIFLIGIMLGYMKSKRREKKSSL

LLLYKDEERLWGEAMKPLPVVSGLRSVQVPLMLNMLQESV

APALSCTLCSMEGDSVSSESSSPDVHLTIQEEGADDELEE

TSETPLNESSEGSSENIHQNS
```

Aspects of the disclosure relate to the observation that KCNE3 and KCNE4 are overexpressed in VT circuits relative to non-VT border zone or uninfarcted myocardium. In some embodiments, the overexpression of KCNE3/KCNE4 leads to an increase in the interactions between KCNE3 and potassium channel α subunits, e.g., KCNQ1, thereby leading to an increase in the concentration of functional potassium channels in VT circuits.

In some embodiments, KCNE3 is overexpressed in VT circuit site by 2-fold relative to an uninfarcted myocardia not having a VT circuit. In some embodiments, KCNE3 is overexpressed in VT circuit site by 1.25-, 1.3-, 1.35, 1.4-, 1.45-, 1.5-, 1.55-, 1.6-, 1.65-, 1.75-1.8-, 1.85-, 1.9-, 1.95-, 2.0-, 2.05-, 2.1-, 2.15-, 2.2-, 2.25-fold or more relative to uninfarcted myocardia (e.g., uninfarcted myocardial tissue or cells), such as myocardia not having a VT circuit. In some embodiments, KCNE3 is overexpressed in VT circuit site by 2-fold relative to a site belonging remote or distal to a VT circuit, e.g., a non-VT myocardial site that belongs to a subject having a VT circuit. In some embodiments, KCNE3 is overexpressed in a VT circuit site by 1.25-, 1.3-, 1.35, 1.4-, 1.45-, 1.5-, 1.55-, 1.6-, 1.65-, 1.75-1.8-, 1.85-, 1.9-, 1.95-, 2.0-, 2.05-, 2.1-, 2.15-, 2.2-, 2.25-fold or more relative to a site belonging remote or distal to a VT circuit, e.g., a non-VT myocardial site that belongs to a subject having a VT circuit.

In some embodiments, KCNE4 is overexpressed in a VT circuit site by 6-fold relative to an uninfarcted myocardia not having a VT circuit. In some embodiments, KCNE3 is overexpressed in VT circuit site by 3-, 3.25-, 3.5, 3.75-, 4-, 4.25-, 4.5-, 4.75-, 5-, 6.25-, 6.5, 6.75-, 7-, 7.25-, 7.5, 7.75-, 8-, 8.25-, 8.5, 8.75-, 9-fold or more relative to an uninfarcted myocardia not having a VT circuit. In some embodiments, KCNE3 is overexpressed in VT circuit site by 6-fold relative to a site belonging remote or distal to a VT circuit, e.g., a non-VT myocardial site that belongs to a subject having a VT circuit. In some embodiments, KCNE4 is overexpressed in a VT circuit by 3-, 3.25-, 3.5, 3.75-, 4-, 4.25-, 4.5-, 4.75-, 5-, 6.25-, 6.5, 6.75-, 7-, 7.25-, 7.5, 7.75-, 8-, 8.25-, 8.5, 8.75-, 9-fold or more relative to a site belonging remote or distal to a VT circuit, e.g., a non-VT myocardial site that belongs to a subject having a VT circuit.

Accordingly, aspects of the disclosure involve methods of identifying ventricular tachycardia (VT) circuits in the heart of a subject, comprising measuring the expression levels of KCNE3 and/or KCNE4 at multiple sites within the heart of the subject, e.g., protein and/or mRNA expression levels; and comparing the relative expression levels of KCNE3 and/or KCNE4 at the multiple sites within the heart of the subject, e.g., comparing expression levels within or proximal to an infarcted scar tissue to expression levels of a control tissue or population of cells; wherein VT circuits in the heart of the subject are identified by elevated expression levels of KCNE3 and/or KCNE4. In some embodiments, methods involve measurement of KCNE3 expression levels. In some embodiments, methods involve measurement of KCNE4 expression levels. In some embodiments, methods involve measurement of both KCNE3 and KCNE4 expression levels.

Expression levels can be quantified using any known or conceivable methodology for quantification of either protein or gene expression. In some embodiments, the methods described herein comprise measuring the expression level of KCNE3 and/or KCNE4 nucleic acids, e.g., mRNA. In some embodiments, the methods described herein comprise measuring the expression level of KCNE3 and/or KCNE4 protein.

In some embodiments, methods comprise measuring the expression level of KCNE3 and/or KCNE4 nucleic acids using quantitative polymerase chain reaction (qPCR). In some embodiments, KCNE3 is quantified in a qPCR assay wherein the assay comprises a sense primer that is specific for KCNE3 (TGCTATGGAGACTAC-CAATGGGACCGAG; SEQ ID NO: 9) and/or an antisense primer that is specific for KCNE3 (CCGCCGCTCCTCAGTCAGGTG; SEQ ID NO: 10). In some embodiments, KCNE4 is quantified in a qPCR assay wherein the assay comprises a sense primer that is specific for KCNE4 (TCCTTCTACGGCATTTTCTTGA; SEQ ID NO: 11) and/or an antisense primer that is specific for KCNE4 (CATGGGCAGCGGCTTCATAG; SEQ ID NO: 12).

In some embodiments, methods comprise measuring the expression level of KCNE3 and/or KCNE4 proteins using enzyme-linked immunosorbent assay (ELISA) and Western blot analysis with anti-KCNE3 and anti-KCNE4 antibodies, respectively. In some embodiments, the amount of KCNE3 and/or KCNE4 may be measured using immunofluorescence with anti-KCNE3 and anti-KCNE4 antibodies, respectively. Anti-KCNE3 antibodies are commercially available from, for example, United States Biological (Catalog No: K0136-33) and Santa Cruz Biotechnology (Catalog No: sc-393841). Anti-KCNE4 antibodies are commercially available from, for example, United States Biological (Catalog No: 128738) and Creative Biolabs (Catalog No: CBMAB-K0530-LY).

Subjects

As used herein, a subject generally refers to a human subject. In some embodiments, a subject may be a human subject, a non-human primate subject, a pig subject, a rodent subject, or any suitable mammalian subject. In some embodiments, a subject has or is suspected of having VT. In some embodiments, a subject has or is suspected of having non-sustained or sustained VT. In some embodiments, a subject has a previous experience with heart disease. In some embodiments, a subject has previously experienced a myocardial infarction. In some embodiments, a myocardial infarction refers to a type of acute coronary syndrome characterized by a sudden or short-term change in symptoms related to blood flow to the heart. In some embodiments, a subject has previously experienced 1, 2, 3, 4, 5, 6, 7, 8, 9, 10, 11, 12, 13, 14, 15, or more myocardial infarctions. In some embodiments, a subject who has experienced a myocardial infarction has a VT circuit. In some embodiments, a subject having VT has at least one VT circuit. In some embodiments, a subject has 1, 2, 3, 4, 5, 6, 7, 8, 9, 10, 11, 12, 13, 14, 15, or more VT circuits. In some embodiments, a subject has an infarct scar. In some embodiments, a subject has 1, 2, 3, 4, 5, 6, 7, 8, 9, 10, 11, 12, 13, 14, 15, or more infarct scars. A subject may be any age or gender.

Heart rates of subjects having VT may vary. In some embodiments, a subject having VT experiences a heart rate of between 80 beats per minute to about 110 beats per minute. In some embodiments, subjects who have VT experience a heart rate that is 100 beats per minute or more. In some embodiments, subjects who have VT experience a heart rate that is about 100, about 110, about 125, about 150, about 170, or about 175 beats per minute. In some embodiments, a subject having VT has experienced a myocardial infarction, coronary heart disease, aortic stenosis, or a cardiomyopathy. In some embodiments, VT results from scarring of a heart muscle tissue, e.g., from a myocardial infarction. In some embodiments, scarred muscle tissue cannot conduct electrical activity, resulting in the generation of a VT circuit surrounding the scarred muscle tissue. In some embodiments, subject having VT comprises a VT circuit. In some embodiments, a VT circuit is characterized by a pattern of sites within the heart comprising short APDs adjacent to sites within the heart comprising long APDs. In some embodiments, a VT circuit is characterized by over-expression of KCNE3 and/or KCNE4.

In some embodiments, a subject having VT is being treated for VT and/or has been previously treated for VT. In some embodiments, treatment options for VT include laser ablation therapy, catheter ablation (e.g., percutaneous catheter-based ablation), cardioversion, external defibrillation, internal defibrillation using an implantable cardioverter-defibrillator, and/or medications such as procainamide, sotalol, or lidocaine.

Treatment of VT

In some embodiments, methods of identification of VT circuits enable downstream targeting of said VT circuits for treatment. In some embodiments, VT circuits may be identified using methods described herein and may be marked for treatment. In some embodiments, methods described herein further comprise targeting of VT circuits for treatment, e.g., in real-time. In some embodiments, treatment options for VT include laser ablation therapy, catheter ablation (e.g., percutaneous catheter-based ablation), cardioversion, external defibrillation, internal defibrillation using an implantable cardioverter-defibrillator, and/or medications such as amiodarone, procainamide, sotalol, or lidocaine. In some embodiments, identification of VT circuits, e.g., using APD measurements, concurrently with laser ablation or catheter ablation therapy.

Targeting KCNE3 and/or KCNE4

Aspects of the disclosure relate to isolated nucleic acids that encode one or more inhibitory nucleic acids (e.g., 1, 2, 3, 4, 5, or more inhibitory nucleic acids. A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

In some aspects, the disclosure relates to isolated nucleic acids comprising an inhibitory nucleic acid that reduce the activity, e.g., expression levels or function, of KCNE3. In some aspects, the disclosure relates to isolated nucleic acids comprising an inhibitory nucleic acid that reduce the activity, e.g., expression levels or function, of KCNE4. In some embodiments, the inhibitory nucleic acid reduces the expression level of KCNE3 and/or KCNE4, thereby reducing the activity of KCNE3 and/or KCNE4. In some embodiments, the inhibitory nucleic acid encodes a protein that functionally competes with KCNE3 and/or KCNE4, thereby reducing the activity of KCNE3 and/or KCNE4.

In some embodiments, an inhibitory nucleic acid is a hairpin-forming RNA, a short interfering RNA (siRNA), or an antisense oligonucleotide (ASO). In some embodiments, a hairpin-forming RNA includes short hairpin RNA (shRNA), microRNA (miRNA) and artificial microRNA (AmiRNA). In some embodiments, inhibitory nucleic acids comprises a region of complementarity to KCNE3 or KCNE3. In some embodiments, an isolated nucleic acid comprises a region of complementarity wherein the region shares at least 50%, at least 60%, at least 70%, at least 80%, at least 90%, at least 95%, or at least 99% complementarity to a KCNE3 or KCNE4 gene sequence. In some embodiments, an inhibitory nucleic acid encodes a protein that functionally competes with KCNE3 and/or KCNE4, e.g., for binding to a protein-protein interaction partner such as KCNQ1.

In some embodiments, the inhibitory nucleic acid is a hairpin-forming RNA that targets KCNE3 or KCNE4. Non-limiting examples of hairpin-forming RNA include short hairpin RNA (shRNA), microRNA (miRNA) and artificial microRNA (AmiRNA). In some embodiments, nucleic acids are provided herein that contain or encode the target recognition and binding sequences (e.g., a seed sequence or a sequence complementary to a target) of any one of the inhibitory RNAs (e.g., shRNA, miRNA, amiRNA) disclosed herein. In some embodiments, the inhibitory nucleic acid is an siRNA, or an antisense oligonucleotide (ASO). In some embodiments, an siRNA that targets a KCNE4 gene (e.g., a sequence encoding an siRNA that targets a KCNE4 gene) is provided in Table 1. The skilled artisan recognizes that in some embodiments, any one or more thymidine (T) nucleotides or uridine (U) nucleotides in a sequence provided herein may be replaced with any other nucleotide suitable for base pairing (e.g., via a Watson-Crick base pair) with an adenosine (A) nucleotide. For example, T may be replaced with U, and U may be replaced with T.

TABLE 1 siRNA that target KCNE4

| Nucleotide sequence | SEQ ID NO: |
|---|---|
| CTGAACATGCTGCAGGAGAGCGTGGCGCC | 25 |
| ATGGCAACGAGTACTTCTACATTCTGGTT | 26 |
| CCGGACGTGCACCTCACCATTCAGGAGGA | 27 |
| GCAGACGAGGAGCTGGAGGAGACCTCGGA | 28 |

Generally, hairpin-forming RNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue. In some embodiments, a uracil (U) nucleobase may be used in place of a thymine (T) nucleobase.

Hairpin-forming RNA are useful for translational repression and/or gene silencing via the RNAi pathway. Due to having a common secondary structure, hairpin-forming RNA share the characteristic of being processed by the proteins Drosha and Dicer prior to being loaded into the RNA-induced silencing complex (RISC). Duplex length amongst hairpin-forming RNA can vary. In some embodiments, a duplex is between about 19 nucleotides and about 200 nucleotides in length. In some embodiments, a duplex is between about between about 14 nucleotides to about 35 nucleotides in length. In some embodiments, a duplex is between about 19 and 150 nucleotides in length. In some embodiments, hairpin-forming RNA has a duplex region that is 19, 20, 21, 22, 23, 24, 25, 26, 27, 28, 29, 30, 31, 32, or 33 nucleotides in length. In some embodiments, a duplex is between about 19 nucleotides and 33 nucleotides in length. In some embodiments, a duplex is between about 40 nucleotides and 100 nucleotides in length. In some embodiments, a duplex is between about 60 and about 80 nucleotides in length.

In some embodiments, the hairpin-forming RNA is a microRNA (miRNA), or artificial microRNA (AmiRNA). A microRNA (miRNA) is a small non-coding RNA found in plants and animals and functions in transcriptional and post-translational regulation of gene expression. An artificial microRNA (AmiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an AmiRNA. In some embodiments, the pri-miRNA scaffold of the AmiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

In some embodiments, isolated nucleic acids provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

The siRNA molecule can be double stranded (e.g. a dsRNA molecule comprising an antisense strand and a complementary sense strand) or single-stranded (e.g. a ssRNA molecule comprising just an antisense strand). The siRNA molecules can comprise a duplex, asymmetric duplex, hairpin or asymmetric hairpin secondary structure, having self-complementary sense and antisense strands.

Aspects of the disclosure relate to isolated nucleic acids encoding a protein that functionally competes with KCNE3 and/or KCNE4. In some embodiments, a protein that functionally competes with KCNE3 and/or KCNE4 is a protein that competes for binding to a potassium voltage-gated alpha subunit, e.g., KCNQ1. In some embodiments, a protein that competes with KCNE3 and/or KCNE4 for binding to a potassium voltage-gated alpha subunit binds with a binding affinity of at least about $10^{-3}$ M $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$M, $10^{-13}$ M, or tighter. In some embodiments, a protein that competes with KCNE3 and/or KCNE4 for binding to a potassium voltage-gated alpha subunit binds to the potassium voltage-gated alpha subunit with a tighter or stronger binding affinity that either KCNE3 or KCNE4. In some embodiments, a protein that competes for binding potassium voltage-gated alpha subunit forms an inactive potassium channel.

The disclosure relates, in some aspects to variants of certain proteins, for example variants of KCNE3 or KCNE4 which compete (e.g., compete with wild-type KCNE3 or KCNE4) for binding potassium voltage-gated alpha subunit. A protein variant may comprise at least 1, 2, 3, 4, 5, 6, 7, 8, 9, 10, 15, 20, 25, 30, 40, 50, or more amino acid mutations (e.g., substitutions) relative to the wild-type protein from which it is derived. In some embodiments, a protein that functionally competes with KCNE3 is a variant of KCNE3. In some embodiments, a protein that functionally competes with KCNE3 is a dominant-negative variant of KCNE3. In some embodiments, a variant of KCNE3 is of human (NCBI Gene ID 10008), pig (e.g., NCBI Gene ID 397168), non-human primate (e.g., NCBI Gene ID 718902), or rodent (e.g., NCBI Gene ID 57442) origin. In some embodiments, a variant of KCNE3 comprises an amino acid sequence that is 99% identical, 95% identical, 90% identical, 85% identical, 80% identical, 75% identical, or 70% identical to a wild-type KCNE3 sequence, e.g., a wild-type sequence encoded by the sequence set forth by any one of GenBank RefSeq Accession Numbers XP_016872541.1, XP_016872540.1, and XP_016872537.1. In some embodiments, a variant of pig KCNE3 is KCNE-V68T (e.g., Val-to-Thr at residue position 68 of pig KCNE3). In some embodiments, a variant of human KCNE3 is KCNE-V72T (e.g., Val-to-Thr at residue position 72 of human KCNE3).

```
KCNE3-V68T
(amino acid sequence from pig;
NCBI Gene ID 397168)
                                  (SEQ ID NO: 29)
METTNGTETWYESLHAVLKALNATLHSNLLCRPGPDHLTEE

RRAGLPGRDDNSYMYILFVMFLFAATTGSLILGYTRSRKVD

KRSDPYHVYIKNRVSMI

KCNE3-V68T (nucleotide sequence from pig)
                                  (SEQ ID NO: 30)
atggaaaccaccaacggcaccgaaacctggtatgaaagcc tgcatgcggtgctgaaagcgctgaacgcgaccctgcatag caacctgctgtgccgcccgggcccggatcatctgaccgaa gaacgccgcgcgggcctgccgggccgcgatgataacagct atatgtatattctgtttgtgatgtttctgtttgcggcgac caccggcagcctgattctgggctatacccgcagccgcaaa gtggataaacgcagcgatccgtatcatgtgtatattaaaa accgcgtgagcatgatt KCNE3-V72T
(amino acid sequence from human;
NCBI Gene ID 10008)
                                  (SEQ ID NO: 31)
METTNGTETWYESLHAVLKALNATLHSNLLCRPGPGLGPDN

QTEERRASLPGRDDNSYMYILFVMFLFAVTTGSLILGYTRS

RKVDKRSDPYHVYIKNRVSMI

KCNE3-V72T
(nucleotide sequence from human)
                                  (SEQ ID NO: 32)
atggaaaccaccaacggcaccgaaacctggtatgaaagc ctgcatgcggtgctgaaagcgctgaacgcgaccctgcat agcaacctgctgtgccgcccgggcccgggcctgggcccg gataaccagaccgaagaacgccgcgcgagcctgccgggc cgcgatgataacagctatatgtatattctgtttgtgatg tttctgtttgcggtgaccaccggcagcctgattctgggc tatacccgcagccgcaaagtggataaacgcagcgatccg tatcatgtgtatattaaaaaccgcgtgagcatgatt
```

In some embodiments, a protein that functionally competes with KCNE4 is a variant of KCNE4. In some embodiments, a protein that functionally competes with KCNE4 is a dominant-negative variant of KCNE4. In some embodiments, a variant of KCNE4 is of human (NCBI Gene ID 23704), pig (e.g., NCBI Gene ID 397167), non-human primate (e.g., NCBI Gene ID 723519), or rodent (e.g., NCBI Gene ID 57814) origin. In some embodiments, a KCNE3 protein comprises an amino acid sequence that is 99% identical, 95% identical, 90% identical, 85% identical, 80% identical, 75% identical, or 70% identical to a wild-type KCNE4 sequence, e.g., a wild-type sequence encoded by the sequence set forth in GenBank RefSeq Accession Number NP_542402.3.

The isolated nucleic acids of the disclosure may further comprise recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid further comprises a region (e.g., a second region, a third region, a fourth region, etc.) comprising a second AAV ITR.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

An isolated nucleic acid as described herein may be located on a vector. As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. In some embodiments, a vector is a plasmid. In some embodiments, an isolated nucleic acid as described herein may be located on an RNA vector.

In some embodiments, a vector is a viral vector, such as an rAAV vector, a lentiviral vector, an adenoviral vector, a retroviral vector, etc. Thus, the term includes cloning and expression vehicles, as well as viral vectors. In some embodiments, vectors are contemplated to be those vectors in which the nucleic acid segment to be transcribed is positioned under the transcriptional control of a promoter.

The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product from a transcribed gene.

A vector or a plasmid may require an origin of replication, e.g., for replication of the vector or plasmid in a host. In some embodiments, a plasmid comprises an origin of replication that is maintained at a high copy number, e.g., from pUC18 or pUC19. In some embodiments, a plasmid comprises an origin of replication that is maintained at a medium copy number, e.g., derived from ColE1, e.g., from pETDuet. In some embodiments, a vector or a plasmid may further comprise a selection marker that ensures maintenance during growth on selective media. In some embodiments, a selection marker is a positive selection marker, e.g., a protein or gene that confers a competitive advantage to a bacterium that contains the selection marker. In some embodiments, a selection marker is a negative selection marker, e.g., a protein or gene that inhibits the growth and/or division of a bacterium that contains the selection marker. In some embodiments, a selection marker is an antibiotic resistance gene.

The isolated nucleic acids of the disclosure may comprise an RNA, e.g., a messenger RNA (mRNA). In some embodiments, an mRNA may comprise a polyA tail at its 3' end, e.g., a poly A-30 tail comprising 30 adenine bases. In some embodiments, a polyA tail comprises about 30, about 50, about 75, about 100, about 150, about 200, or about 300 adenine bases. In some embodiments, an mRNA may comprise a 5' cap, e.g., a GAG cap or a 7-methylguanosine cap. In some embodiments, an mRNA may further comprise at least one untranslated region. In some embodiments, an mRNA may be single-stranded.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein.

An isolated nucleic acid comprising an inhibitory nucleic acid encoding a protein that functionally competes with KCNE3 and/or KCNE4 may be positioned at any suitable location of the isolated nucleic acid that will enable expression of the inhibitory nucleic acid, an optional selectable marker protein, and/or an optional reporter protein.

It should be appreciated that in cases where a nucleic acid encodes more than one polypeptide, each polypeptide may be positioned in any suitable location within the transgene. For example, a nucleic acid encoding a first polypeptide may be positioned in an intron of the transgene and a nucleic acid sequence encoding a second polypeptide may be positioned in another untranslated region (e.g., between the last codon of a protein coding sequence and the first base of the poly-A signal of the transgene).

A "promoter" refers to a DNA sequence recognized by the synthetic machinery of the cell, or introduced synthetic machinery, required to initiate the specific transcription of a gene. The phrases "operatively linked," "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an RNA pol II promoter. In some embodiments, a promoter is an RNA pol III promoter, such as U6 or H1. In some embodiments, a promoter is an RNA pol II promoter. In some embodiments, a promoter is a chicken β-actin (CBA) promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In some embodiments, nucleic acids comprising tissue-specific promoters provide tissue-specific gene expression capabilities. Such tissue-specific promoter sequences are well known in the art. In some embodiments, a tissue-specific promoter is a muscle-specific promoter, e.g., a cardiac-specific promoter. Exemplary muscle-specific promoter sequences include, but are not limited to a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, a myosin light chain-2v (MLC-2v) promoter, an α-cardiac actin promoter, a cardiac Troponin T (cTnT) promoter, cardiac Troponin C promoter (cTnC), sodium-calcium exchanger promoter (NCX) or others which will be apparent to a skilled artisan.

In some aspects, the disclosure relates to small molecules or compounds that reduce the activity, e.g., expression levels or function, of KCNE3. In some aspects, the disclosure relates to small molecules or compounds that reduce the activity, e.g., expression levels or function, of KCNE4. In some embodiments, the small molecule reduces the expression level of KCNE3 and/or KCNE4, thereby reducing the activity of KCNE3 and/or KCNE4. In some embodiments, the small molecule functionally competes with KCNE3 and/or KCNE4, thereby reducing the activity of KCNE3 and/or KCNE4. In some embodiments, the small molecule is an organic small molecule that is able to reduce the activity of KCNE3 and/or KCNE4. In some embodiments, the small molecule specifically binds to KCNE3 and/or KCNE4. In some embodiments, the small molecule specifically binds to a protein-protein interaction partner of KCNE3 and/or KCNE4, e.g., KCNQ1. In some embodiments, the small molecule disrupts the binding interaction between KCNE3 and KCNQ1. In some embodiments, the small molecule disrupts the binding interaction between KCNE4 and KCNQ1.

Recombinant Adeno-Associated Viruses (rAAVs)

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV1, AAV2, AAV3, AAV4, AAV5, AAV6, AAV7, AAV8, AAVrh8, AAV9, AAV10, AAVrh10, and AAV.PHP.B. In some embodiments, an AAV capsid protein is of a serotype derived from a non-human primate, for example AAVrh8 serotype. In some embodiments, an AAV capsid protein is of a serotype that targets (e.g., has tropism for) cardiac tissue. Examples of AAV capsid proteins that target cardiac tissue include AAV1, AAV2, AAV6, AAV8, AAV9, and AAV10.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a transgene (e.g., a mutant variant of KCNE3 or KCNE4). In some embodiments, the host cell is a mammalian cell, a yeast cell, a bacterial cell, an insect cell, a plant cell, or a fungal cell.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an AAV vector (comprising a transgene flanked by ITR elements) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. In some embodiments, a host cell is a cardiac cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

Methods for Regulating Target Gene Expression

Methods for regulating target gene (e.g., KCNE3 and KCNE4) expression in a cell or subject are provided by the disclosure. In some embodiments, the methods involve administering to a cell, e.g., a myocardial cell, or a subject, e.g., a subject having VT, an isolated nucleic acid comprising an inhibitory nucleic acid that targets a gene encoding an KCNE3 and KCNE4 protein. In some embodiments, an inhibitory protein is an shRNA, an siRNA, microRNA, artificial microRNA (amiRNA), or an antisense oligonucleotide (ASO). In some embodiments, the methods involve administering to a cell or a subject an isolated nucleic acid comprising an inhibitory nucleic acid that encodes a protein that functionally competes with KCNE3 and KCNE4 protein, e.g., a variant of KCNE3 or KCNE4, e.g., KCNE3-V68T or V72T. In some embodiments, the isolated nucleic acid further comprises a rAAV, optionally wherein the serotype of the capsid protein is selected from the group consisting of: AAV1, AAV2, AAV3, AAV4, AAV5, AAV6, AAV7, AAV8, AAVrh8, AAV9, AAV10, AAVrh10, or AAV.PHPB. In some embodiments, the rAAV comprises an AAV2 or AAV6 capsid protein.

In some aspects, the disclosure provides methods of modulating (e.g., increasing, decreasing, etc.) activity of a target gene in a cell or a subject. In some embodiments, the modulating is decreasing expression of a target gene (e.g., KCNE3 or KCNE4) in a cell or subject. In some embodiments, expression of a target gene (e.g., KCNE3 or KCNE4) is decreased by at least 5%, 10%, 15%, 20%, 25%, 30%, 35%, 40%, 45%, 50%, 55%, 60%, 65%, 70%, 75%, 80%, 85%, 90%, 95%, or 100% relative to a control, e.g., basal expression level of a target gene. In some embodiments, expression of a target gene (e.g., KCNE3 or KCNE4) is decreased by at least 1-fold, 1.5-fold, 2-fold, 3-fold, 4-fold, 5-fold, 6-fold, 7-fold, 8-fold, 9-fold, 10-fold, 20-fold, 30-fold, 40-fold, or 50-fold relative to a control, e.g., basal expression level of a target gene. In some embodiments, the modulating is decreasing functional activity of a target protein (e.g., KCNE3 or KCNE4) in a cell or subject, e.g., by competing with KCNE3 for binding to a potassium voltage-gated alpha subunit. In some embodiments, functional activity of a target protein (e.g., KCNE3 or KCNE4) is decreased by at least 5%, 10%, 15%, 20%, 25%, 30%, 35%, 40%, 45%, 50%, 55%, 60%, 65%, 70%, 75%, 80%, 85%, 90%, 95%, or 100% relative to a control, e.g., basal expression level of a target protein. In some embodiments, functional activity of a target protein (e.g., KCNE3 or KCNE4) is decreased by at least 1-fold, 1.5-fold, 2-fold, 3-fold, 4-fold, 5-fold, 6-fold, 7-fold, 8-fold, 9-fold, 10-fold, 20-fold, 30-fold, 40-fold, or 50-fold relative to a control, e.g., basal expression level of a target protein.

In some embodiments, a cell is a mammalian cell, such as a human cell, non-human primate cell, cat cell, mouse cell, dog cell, rat cell, hamster cell, etc. In some embodiments, a cell is a myocardial cell. In some embodiments, a cell is in a subject (e.g., in vivo).

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes are formulated in buffer solutions such as phosphate-buffered saline solutions, liposomes, micellar structures, and capsids.

In some embodiments, compositions herein may include separately one or more of isolated nucleic acids provided herein. In some embodiments, compositions are formulated with any pharmaceutically acceptable carrier. In some embodiments, compositions are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a composition is lyophilized to extend its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrolidone), or a collapse temperature modifier (e.g., dextran, ficoll, or gelatin).

Administering a composition comprising an isolated nucleic acid as described by the disclosure to a cell or subject, in some embodiments, results in decreased expression of a target gene (e.g., KCNE3 or KCNE4). In some embodiments, administering a composition comprising an isolated nucleic acid as described by the disclosure to a cell or subject, in some embodiments, results in decreased function of a target protein (e.g., KCNE3 or KCNE4). Thus, in some embodiments, compositions and methods described by the disclosure are useful for treating conditions, e.g., VT and complications thereof, resulting from overexpression of KCNE3 and KCNE4 proteins. In some embodiments, dysfunction of KCNE3 and KCNE4 proteins or aberrant (e.g., increased or decreased, relative to a normal subject) expression of KCNE3 and KCNE4 genes is caused by VT, optionally resulting from a previous myocardial infarction.

Aspects of the disclosure relate to a subject or cell that is characterized by aberrant (e.g., increased or decreased, relative to a healthy, normal cell or subject) expression of a gene encoding an KCNE3 or KCNE4 protein. In some embodiments, "decreased" expression or activity of a gene is measured relative to expression or activity of that gene in a cell or subject who has not been administered one or more isolated nucleic acids or compositions as described herein. In some embodiments, "decreased" expression or activity of a gene in a VT circuit is measured relative to expression or activity of that gene in a non-VT tissue. Methods of measuring gene expression or protein levels are known in the art and include, for example, quantitative PCR (qPCR), Western Blot, mass spectrometry (MS) assays, etc.

In some embodiments, administration of an isolated nucleic acid or composition as described by the disclosure results in a reduction of KCNE3 or KCNE4 expression and/or activity in a subject between 1.25-fold and 50-fold (e.g., 1.25-fold, 2-fold, 5-fold, 10-fold, 50-fold, etc.) relative to the KCNE3 or KCNE4 expression and/or activity of a subject who has not been administered one or more compositions described by the disclosure. In some embodiments, administration of an isolated nucleic acid or composition as described by the disclosure results in a reduction of KCNE3 or KCNE4 expression and/or activity in a VT circuit between 1.25-fold and 50-fold (e.g., 1.25-fold, 2-fold, 5-fold, 10-fold, 50-fold, etc.) relative to the KCNE3 or KCNE4 expression and/or activity of non-VT tissue.

Modes of Administration

The isolated nucleic acids, rAAVs, and compositions of the disclosure may be delivered to a subject in compositions according to any appropriate methods known in the art. For example, an rAAV, preferably suspended in a physiologically compatible carrier (e.g., in a composition), may be administered to a subject, e.g., a subject having VT, e.g., a subject having a VT circuit identified by the methods described herein.

Delivery of the compositions herein to a mammalian subject may be by, for example, intramuscular injection or by administration into the bloodstream of the mammalian subject. Administration into the bloodstream may be by injection into a vein, an artery, or any other vascular conduit. In some embodiments, the compositions are administered into the bloodstream by way of isolated limb perfusion, a technique well known in the surgical arts, the method essentially enabling the artisan to isolate a limb from the systemic circulation prior to administration of the compositions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. In some embodiments, a composition as described in the disclosure are administered by intravenous injection. In some embodiments, compositions are administered by intracardiac injection. In some embodiments, compositions are administered by transcutaneous injection, intravascular injection, intramuscular injection, cardiopulmonary bypass, or a combination thereof.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

The compositions are administered in sufficient amounts to transfect the cells and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents that modulate expression or function of KCNE3 and/or KCNE4 as described herein, along with instructions describing the intended application and the proper use of these agents. In some embodiments, such kits may include one or more agents that allow for determination of expression levels or functional activity of KCNE3 and/or KCNE4 as described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for constructing an AAV vector as described herein. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: Analyzing Gene Expression Circuits in VT, Non-VT Border Zone, and Uninfarcted Cardiac Tissues To identify elements unique to ventricular tachycardia (VT) circuits, gene expression and electrophysiological function was assessed within VT circuits and compared to non-VT border zone tissues and uninfarcted myocardium. These studies were performed in a validated, clinically relevant porcine model of healed, post-infarct VT. In an initial cohort of 5 pigs with healed anterior-septal left ventricular myocardial infarctions, VT circuit expression levels were evaluated for key determinants of cardiac conduction and repolarization. To accomplish this, VT circuit tissues were identified and harvested, and mRNA expression was compared in the VT circuit, non-VT border zone, and uninfarcted myocardium regions. VT circuit locations were identified using established clinical electrophysiology techniques of activation and entrainment mapping. An example of the VT circuit identification process is shown in FIG. 1.

Figure 2A:
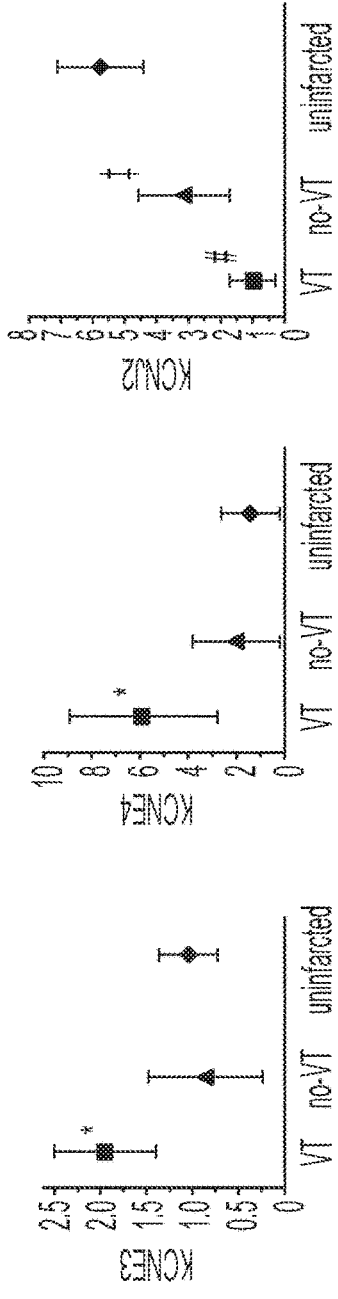
FIGS. 2A-2C shows graphs depicting mRNA expression of the principal cardiac ion channels and connexin 43 between the mapped ventricular tachycardia (VT) site (square), a site harvested on the opposite side of the infarct scar from the VT site (triangle) and uninfarcted basal lateral myocardium (diamond).
Figure 2B:
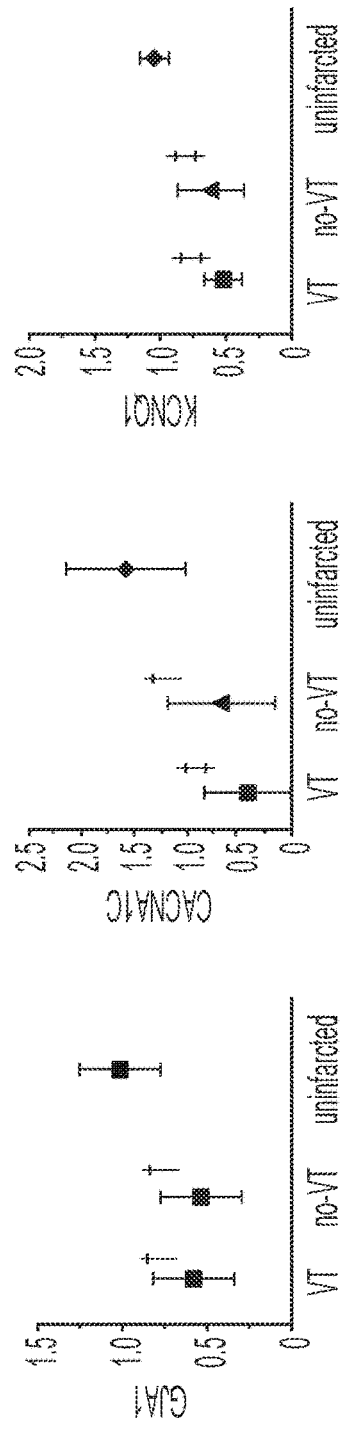
Figure 2C:
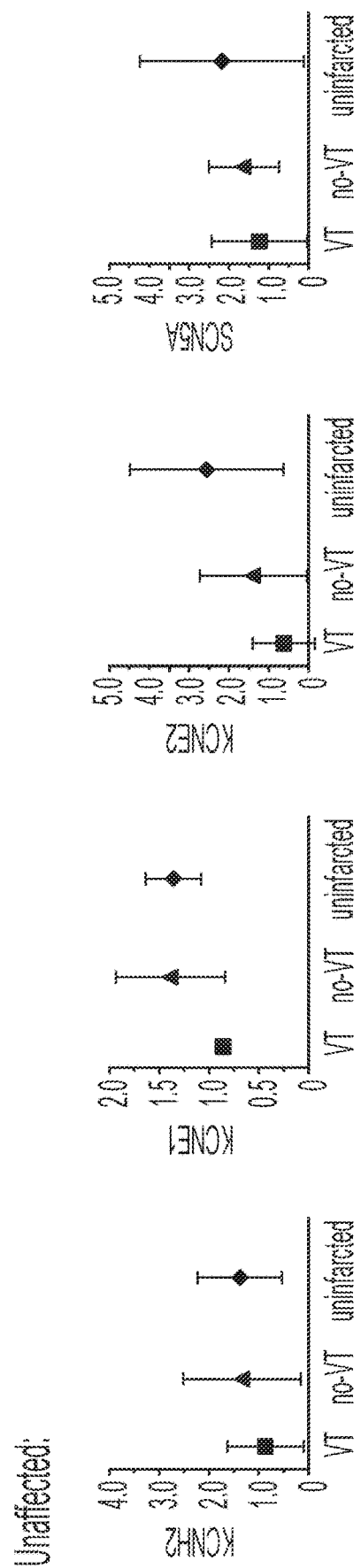

In each of the animals for this portion of the study, there was only a single VT morphology per animal, and that morphology was repeatedly and reliably induced with programmed electrical stimulation techniques. After activation mapping to identify a suspected VT circuit, entrainment mapping criteria were tested and fulfilled to identify the protected isthmus where diastolic activation occurred (FIG. 1). The VT isthmus was then harvested from each animal, and mRNA expression was compared in VT-isthmus tissues to non-VT border zone tissues harvested from the opposite side of each scar and to uninfarcted myocardium from basal lateral left ventricular sites remote from the infarcted region (FIG. 2). Potassium channel beta-subunits KCNE3 and KCNE4 and alpha-subunit KCNJ2 were uniquely upregulated at VT sites relative to non-VT border zone or uninfarcted myocardium, demonstrating the import of these ion channel subunits in the VT mechanism. There were also uniform reductions in border zone expression of GJA1, CACNA1C and KCNQ1 at both VT and non-VT sites, indicating that expression of these genes was altered diffusely throughout border zone but not uniquely inside VT circuits. There were no differences between subgroups in expression levels of the ion channel subunits KCNH2, KCNE1, KCNE2 or SCN5A, indicating that these ion channels were not affected by the infarction.

Example 2: VT Sites Display Heterogeneous Action Potential Duration (APD) Compared to Non-VT Sites In vivo bipolar electrogram and monophasic action potential (MAP) records, optical mapping of perfused cardiac ventricular tissue wedges, and patch clamp analysis of isolated ventricular myocytes were used to identify unique functional elements of VT circuits in a second cohort consisting of 10 animals with reproducibly inducible post-infarct VT and 5 animals with healed infarcts but absolutely no VT by repeated weekly in vivo testing and post-sacrifice ex vivo evaluation.

Figure 3A:
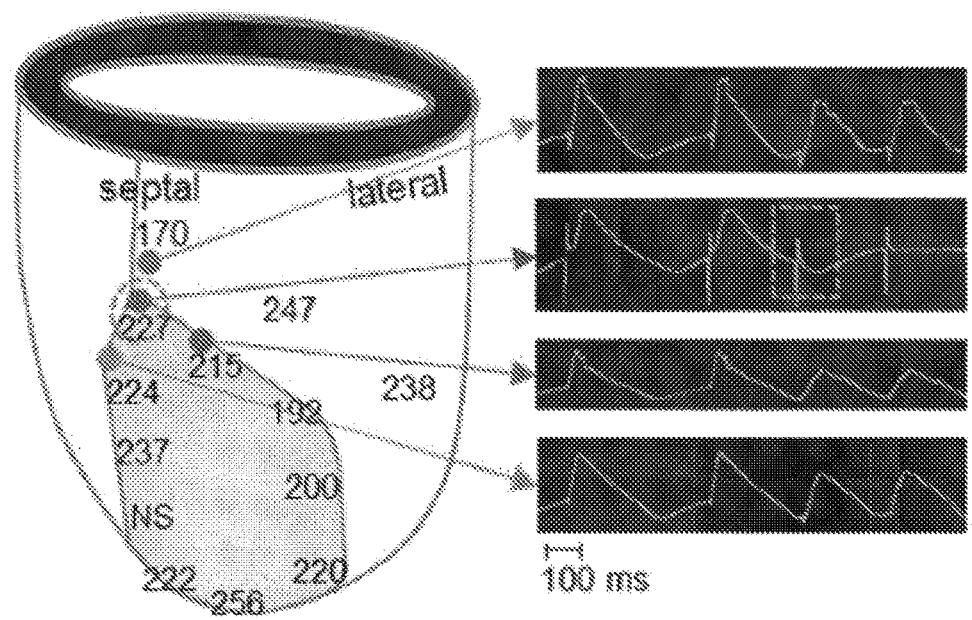
FIGS. 3A-3C. present an electrogram analysis from epicardial monophasic action potential and bipolar electrogram recordings during an in vivo electrophysiology study.
Figure 3B:
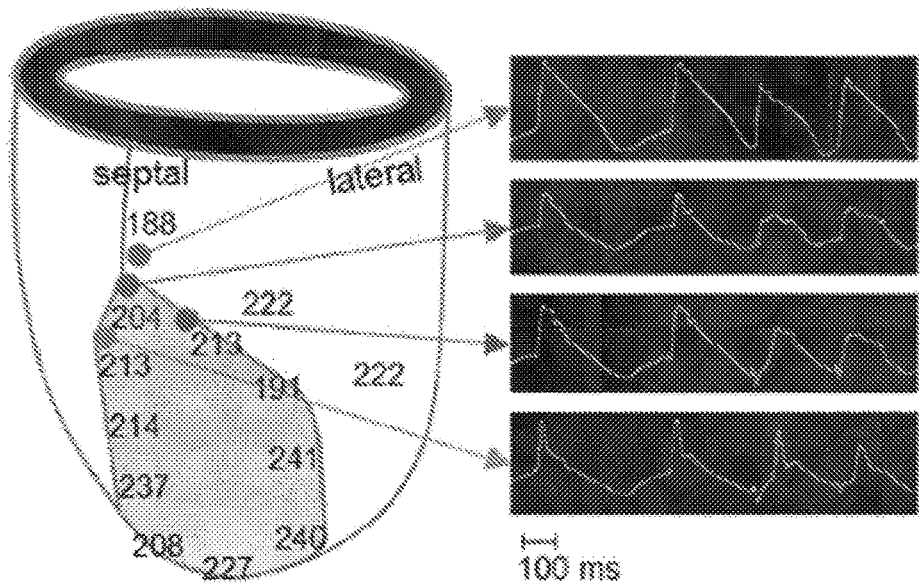

In vivo assessment of action potential duration (APD) on MAP recordings showed a consistent pattern of relatively shorter APDs adjacent to relatively longer APDs at VT circuit locations in the VT animals (FIG. 3A). The no-VT animals had no discernable APD pattern and less overall APD heterogeneity across the infarct scar border (FIG. 3B).

The functional consequences of these localized APD heterogeneities became apparent with abrupt change in the pacing rate; the areas with shorter APDs continued to conduct each paced beat after the pacing cycle length switched from 400 to 250 ms (box in FIG. 3A), but the areas with longer APDs had transient conduction delay or block at the faster cycle length. Transient conduction block in a myocardial tissue tract adjacent to another tract with continued conduction is a classical condition for reentry.

Figure 3C:
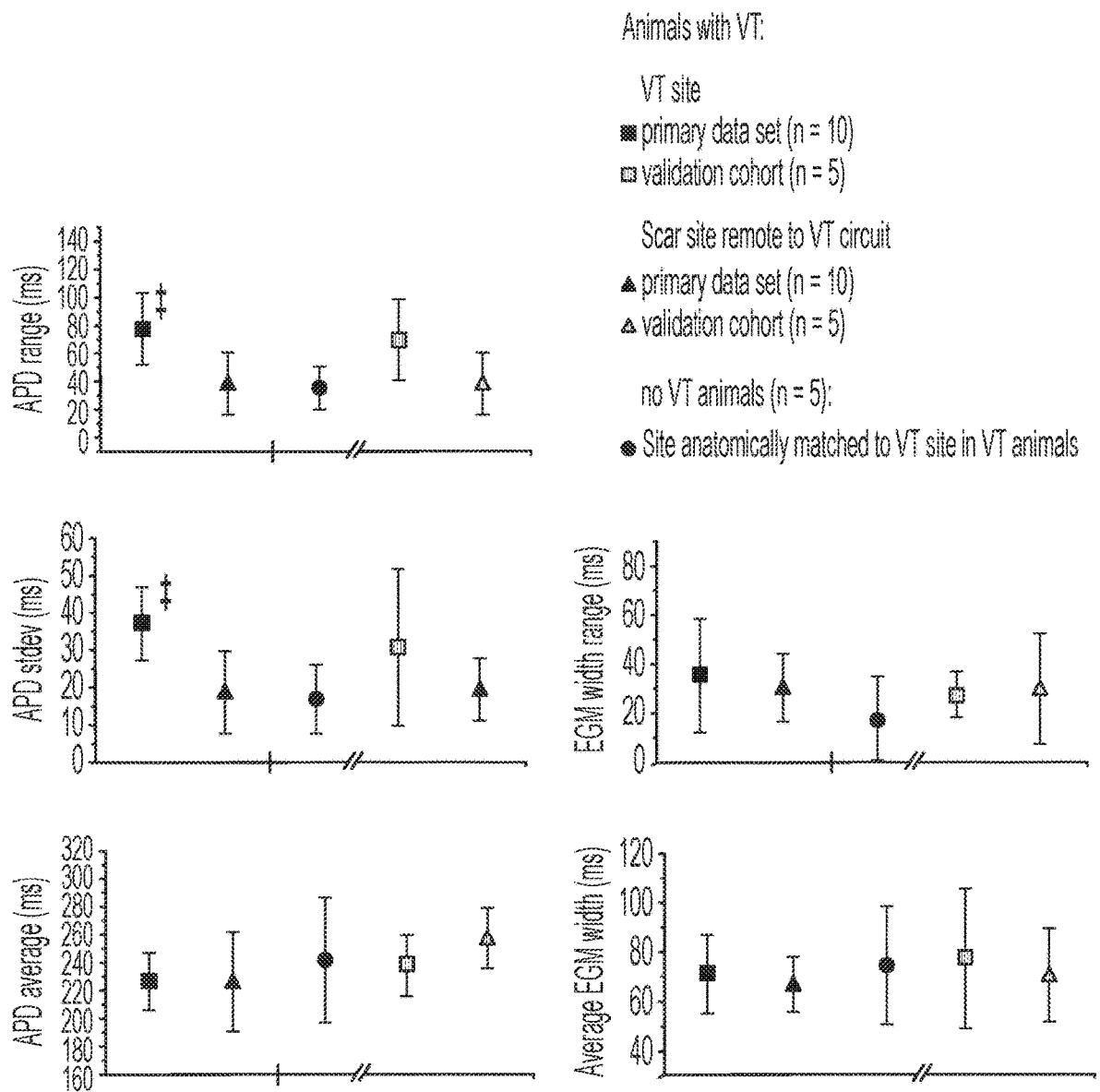

Conduction heterogeneity was assessed in the infarct border zone by measuring electrogram width and previously described electrogram characteristics of split, fractionated and low amplitude signals, and no significant differences were found between the VT and no-VT animals. Conduction was impaired throughout the infarct scar border in all animals, indicating that slow, heterogeneous conduction was a ubiquitous border zone property. To connect these observations specifically to the VT circuits, APD and electrogram characteristics of the mapped VT circuit sites were compared to border zone areas remote to VT circuits in the VT animals and to paired anatomical locations in no-VT animals. There were no differences in average APD, average electrogram width, or electrogram-width range between groups. The APD range was significantly greater at the VT sites, verifying greater APD heterogeneity specifically at sites where VT was found (FIG. 3C).

Example 3: Optical Mapping of VT and Non-VT Tissues Confirms APD Heterogeneity in VT Tissues After completing the in vivo study in the second cohort of animals, the hearts were harvested and the infarct border zone tissues were subdivided into myocardial tissue wedges for optical mapping of electrical activity and for cell isolation and patch clamp analysis. In the VT animals, since optical mapping allowed identification and assessment of VT circuits, myocardial tissue wedges used in the optical mapping experiments included both those with and without in vivo mapped VT circuits. Since patch clamp analysis did not afford the possibility of mapping and identifying VT circuits, only tissue wedges were used for cell isolation and patch clamp analysis that came from regions where a VT circuit was mapped in vivo. In the no-VT animals, wedges came from the same anatomical locations as those taken from the VT animals.

Figure 4A:
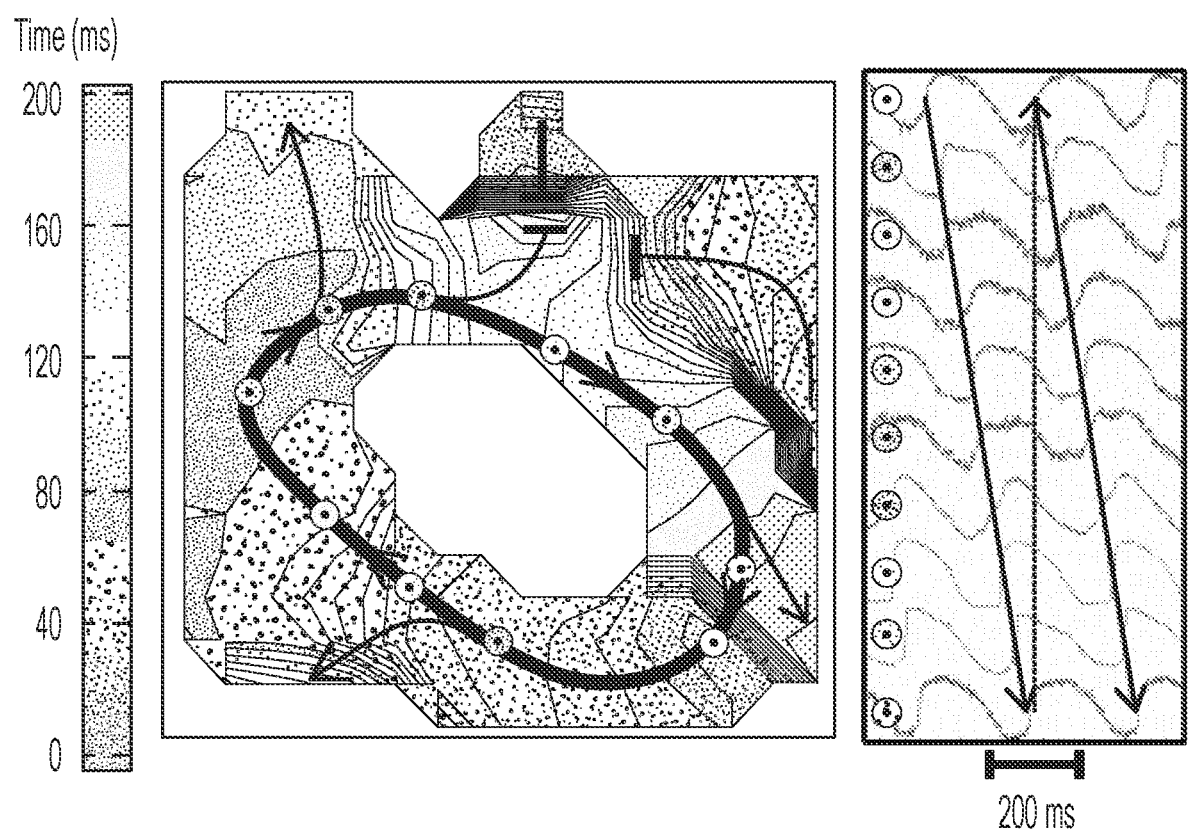
FIGS. 4A-4E show optical mapping of VT circuits induced in myocardial tissues wedges taken from healed infarct scar tissues.
Figure 4B:
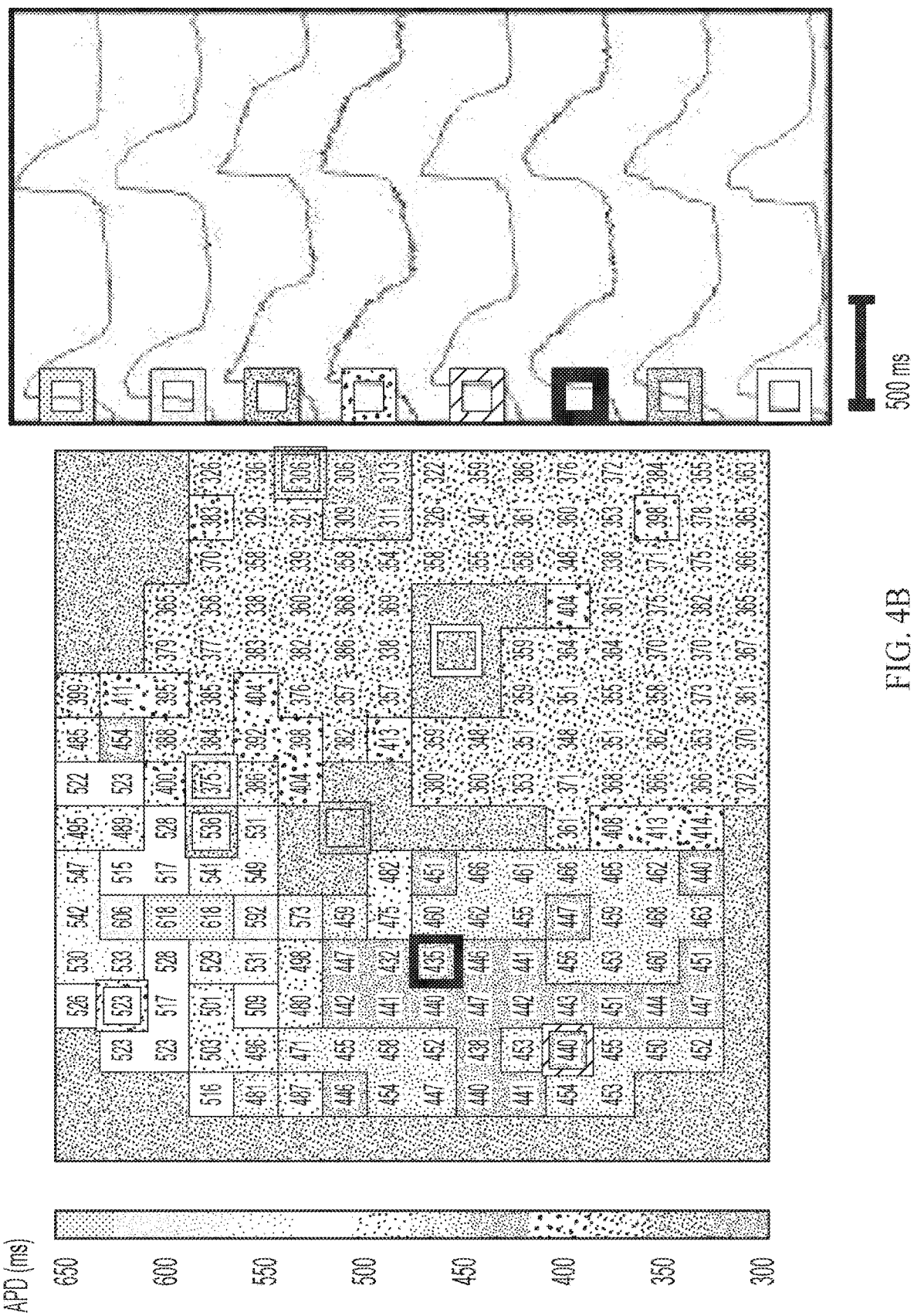
Figure 4C:
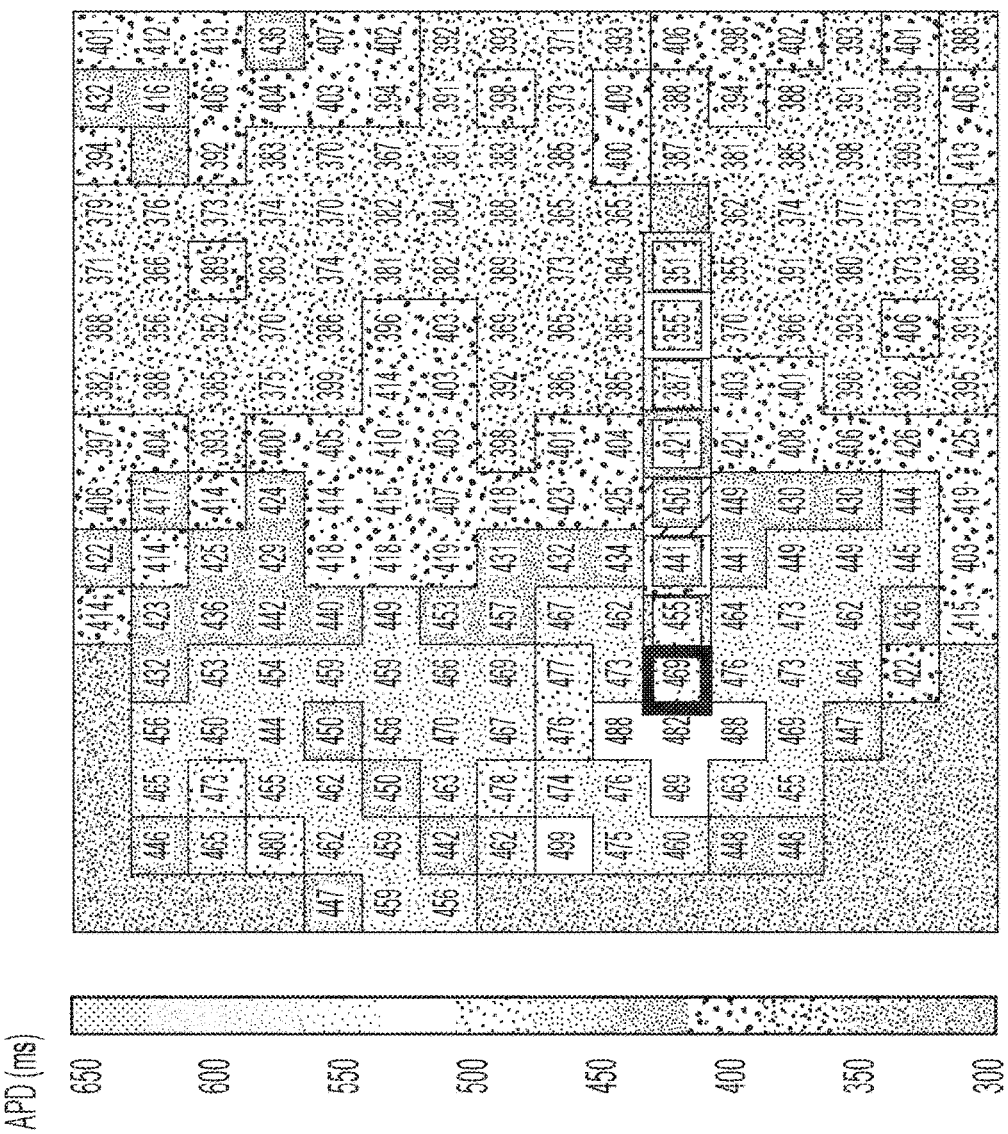
Figure 4C:
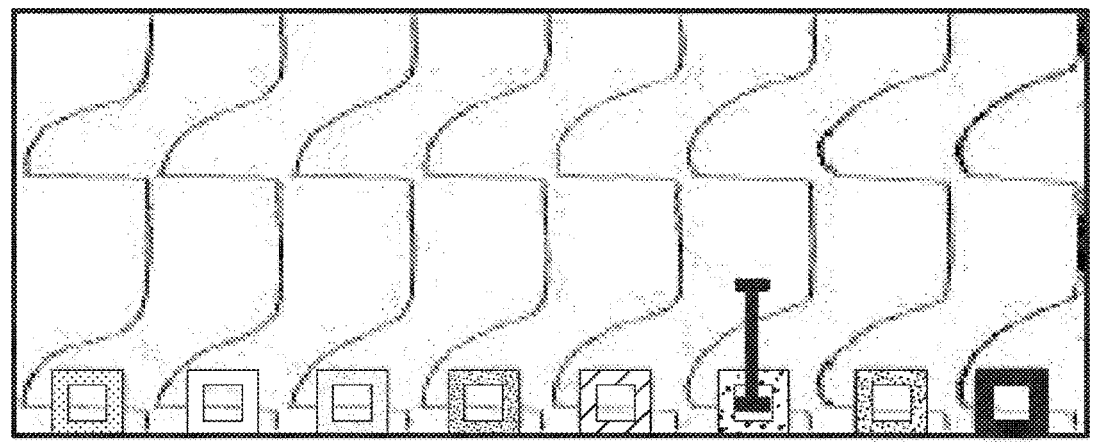
Figure 4D:
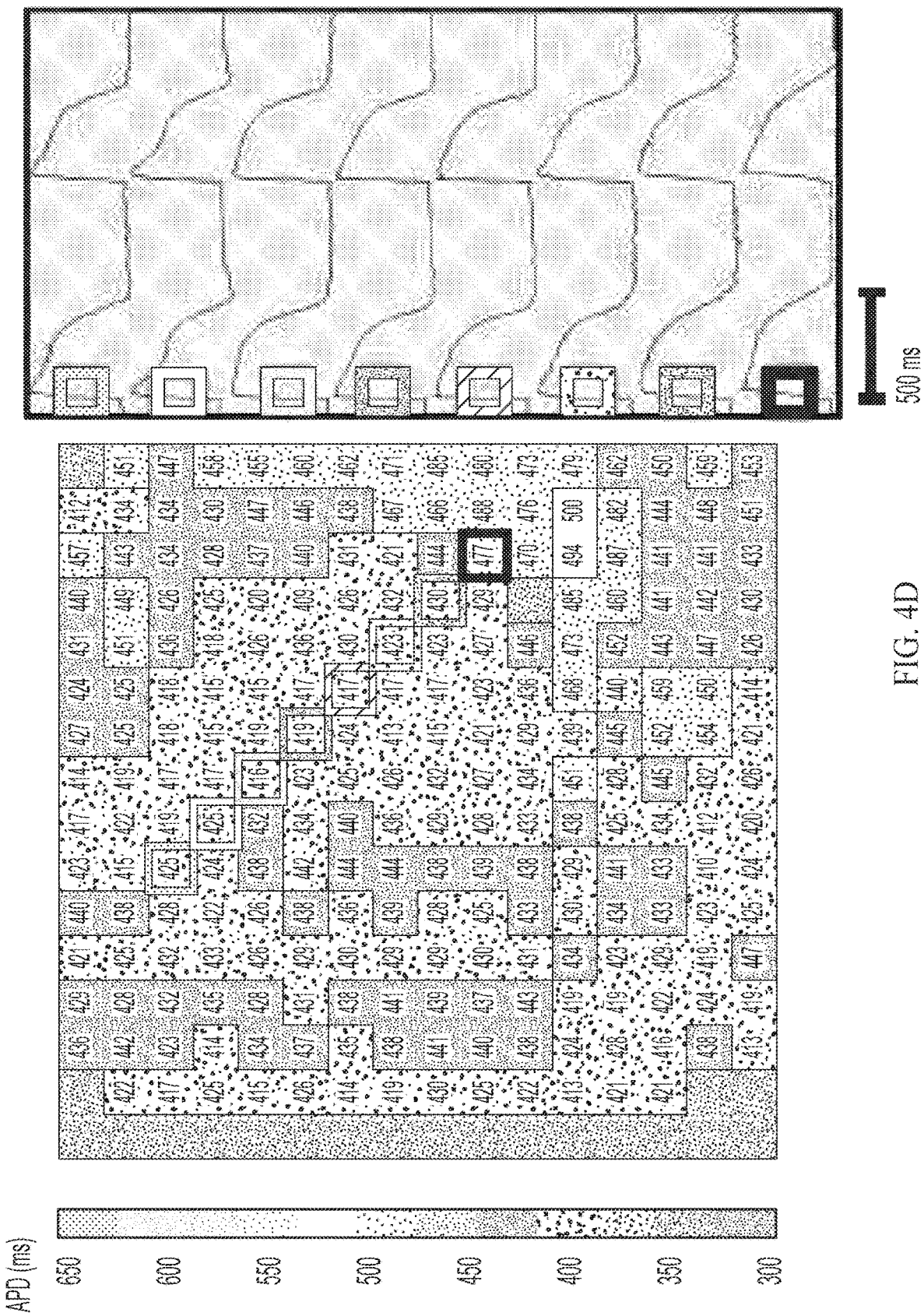

In the optical mapping experiments, complete VT circuits were identified along single surfaces of tissue wedges in 4 VT animals (2 from the transmural surface of left ventricle (LV) free wall wedges, 1 from the transmural surface of the ventricular septum, and 1 from the LV free wall endocardium). All the observed VT circuits had a tract of cells with short APDs adjacent to a tract with long APDs during steady rate pacing that corresponded to the 2 limbs of the reentrant circuit during VT (FIG. 4A-B). In the remaining 45 optical maps obtained from border zone tissue wedges in VT-group animals, 33 maps came from wedges that had inducible VT, and 12 came from wedges where VT could not be induced. In the wedges where VT was induced but the full circuit was not visible, 11 maps had focal areas of either shorter or longer APDs that were not adjacent to each other, 1 had progressively increasing APD from the endocardial to the epicardial edges and 21 had no APD gradients (FIG. 4C). In the 12 maps from uninducible wedges in VT group animals, no APD gradients were found. Similarly, in the 20 optical maps from infarct border zone tissue wedges for the no-VT group, no APD gradients were found (FIG. 4D). To quantify the APD heterogeneity in the optical mapping data, the range and standard deviation of APD measurements was assessed across each mapping field. Both measures were significantly longer in the mapping fields with VT circuits (FIG. 4E).

Figure 4E:
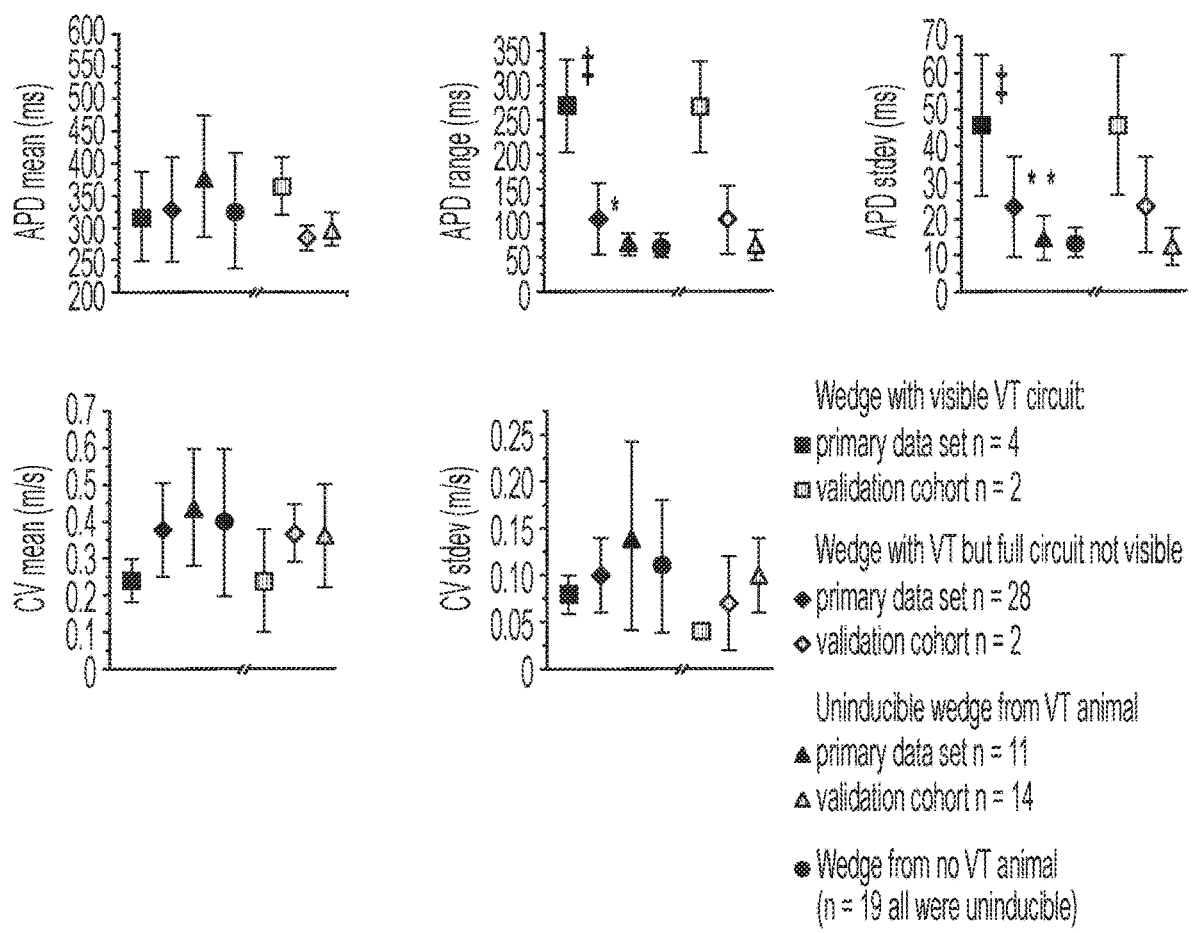

In contrast to the repolarization changes that were unique to VT circuits, conduction velocity was depressed in all infarct border zone wedges of all animals, and there were no significant differences when comparing overall conduction velocity or measures of conduction velocity heterogeneity between fields with complete VT circuits, incomplete VT circuits or non-inducible wedges in the VT animals or in comparison to the infarct border zone wedges in the non-VT animals (FIG. 4E).

Figure 5A:
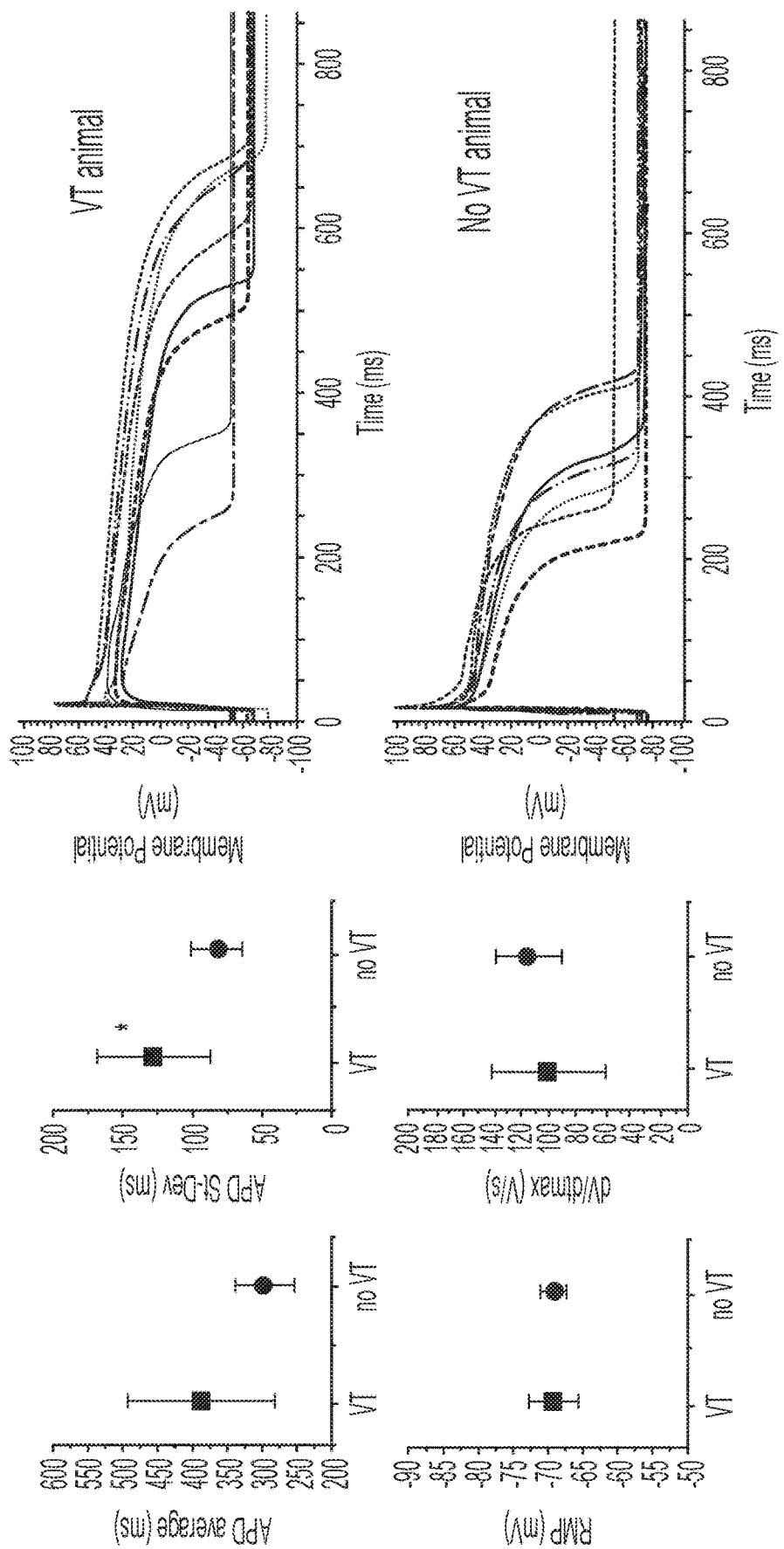
Figure 6A:
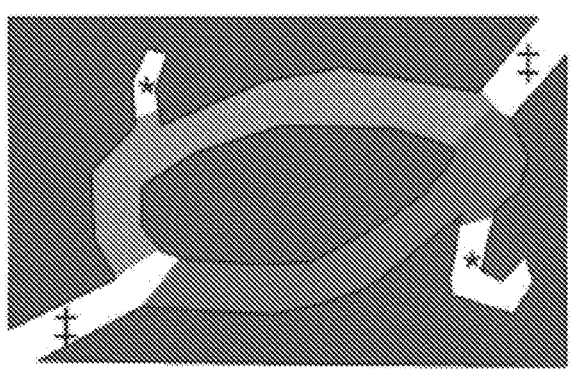
FIGS. 6A-6B is a schematic illustrating a VT mechanism.
Figure 6B:
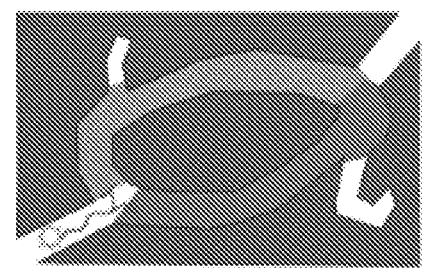
Figure 6B:
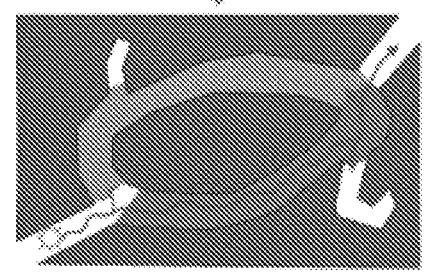
Figure 6B:
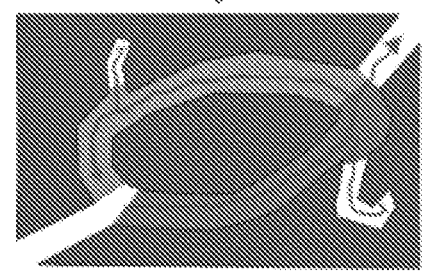
Figure 6B:
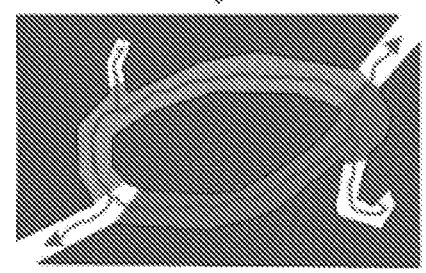
Figure 6B:
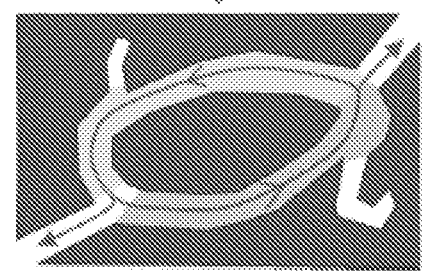

Example 4: Patch Clamp Studies Show Heterogeneous Repolarizing Potassium Current in VT Tissues Unlike the optical mapping findings where different parts of the VT circuits could be visualized and measured, patch clamp analyses could only come from myocytes that were harvested from the area where VT circuits were found. Viable myocytes were isolated from myocardial wedges of 8 out of the 10 animals with VT and all 5 animals without VT. In myocytes isolated from the general region of the VT circuits, APDs were more heterogeneous in the VT animals compared to myocytes isolated from anatomically similar areas of the no-VT animals (FIG. 5A). There were no differences between groups in resting membrane potential or maximum rate of rise of the action potential upstroke; both were impaired relative to reported normal values, but they were similarly impaired. The repolarizing potassium current (IKs) was reduced in the VT animals compared to the no-VT animals (FIG. 5B). Other repolarizing potassium currents (IKr and IK1) were not significantly different between groups. The lack of between-group differences in resting membrane potential or IK1 indicates that the molecular changes observed for KCNJ2 at the VT site may not have functional implications.

In looking at individual current tracings (FIG. 5C), 5 of the 8 VT animals had noticeably heterogeneous IKs, with some cells having increased IKs that had an atypical instantaneous component to the current, some cells having relatively normal IKs amplitude and morphology, and other cells from the same myocardial region having decreased or non-existent IKs. In the remaining 3 VT animals, only the reduced IKs phenotype was present. By comparison, in the 5 non-VT animals, 1 animal had cells with only the small IKs phenotype and the other 4 had normal appearing IKs size and morphology.

Example 5: Heterogeneous APDs and Repolarization Potassium Current are Confirmed in a Retrospective Data Set The in vivo electrophysiology and optical mapping results from the VT animals in the current study were compared to stored data from a previously reported cohort of VT animals to assess the reproducibility of the findings. VT inducibility and conduction velocity results in a control group of post-infarct animals that had a healed myocardial infarction, a 4-week post-MI sham gene transfer procedure (intracoronary infusion of vascular endothelial growth factor, nitroglycerin and adenosine in saline) and then 5-week post-MI sacrifice study were assessed. The 5 sham gene transfer animals were also re-evaluated with optical mapping data. A similar repolarization patterns to those identified in the primary cohort for the current study were studied. VT circuit-specific repolarization heterogeneity was found both in vivo (FIG. 3C) and in optical mapping experiments (FIG. 4E). In this validation cohort, 2 additional wedges with the full VT circuit visible on a single mapped surface of the wedge, and both had tracts of myocytes with long APDs adjacent to tracts with short APDs like the 4 VT circuits included in the primary study were identified.

VT circuits reproducibly occur in regions of infarct scar border where surviving myocardial tissues with long APDs are adjacent to myocardium with short APDs. The areas with short APDs adapt to abrupt changes in activation rate, allowing continued conduction at faster rates, and the areas with long APDs have transient conduction block when activation rate changes abruptly. The heterogeneities in APD are caused by changes in the repolarizing potassium current IKs, and they occur where there is upregulation of potassium channel β subunits KCNE3 and KCNE4. These data indicate that the sequence of events for initiation and maintenance of VT is that a critically timed premature beat conducts through surviving strands of myocardium within the infarcted region to a proximal junction between short and long APD tissues. The depolarization wavefront is able to continue conducting through the myocyte strand with short APDs and it blocks in the still refractory strand with long APDs. If conduction time through the short APD strand is sufficiently long (made more likely by the diffusely impaired conduction throughout myocardial border zone), the depolarization wavefront would meet excitable tissue at the distal junction between short and long APD tissues, allowing it to conduct back up the long APD strand and to then continue in a reentrant manner down the short APD strand and back up the long APD strand (FIG. 6).

The present data identify a unique and potentially exploitable element of VT circuits in hearts with healed infarct scars. Reentrant VT circuits are composed of impaired conduction that is a diffuse infarct border zone property and discrete, adjacent areas with relatively longer and shorter APDs that is a unique VT circuit property. The heterogeneous repolarization creates a substrate supportive of reentrant arrhythmias. Data described herein indicate that upregulation in the potassium channel β subunits, KCNE3 and KCNE4, are related to the heterogeneities in repolarization. KCNE3 increases IKs and shortens repolarization time; KCNE4 decreases IKs, delaying repolarization.

Materials and Methods:

The primary study included a total of 20 Yorkshire pigs (25-30 kg): 5 animals had molecular analysis of harvested ventricular tachycardia (VT) circuit tissues and 15 animals had in vivo assessment of electrophysiology followed by ex vivo optical mapping and patch clamp analysis. All animals underwent an initial myocardial infarction/defibrillator implantation procedure. They had non-invasive electrophysiology study performed weekly thereafter until undergoing a sacrifice invasive electrophysiology study and VT mapping procedure 5 weeks after infarction.

In addition to the prospectively collected data from 20 pigs in the primary study, data from a previously reported cohort of 5 pigs was retrospectively analyzed to validate the observations. Animals underwent the same initial myocardial infarction/defibrillator implantation procedure, had weekly electrophysiology study and a 5-week post-MI sacrifice study. In addition, the retrospectively analyzed validation cohort had a sham gene transfer procedure 4 weeks post-MI where they had intracoronary infusion of vascular endothelial growth factor, adenosine, and nitroglycerin in saline.

Myocardial Infarction and Defibrillator Implantation.

After overnight fasting, each animal was sedated with telazol, ketamine and xylazine (1.5-2.5 mg/kg of each). After a sufficient level of sedation was achieved, the animal was intubated, and then anesthesia was maintained with inhaled isoflurane (0.5-2.5%). The intubated, anesthetized animal was transported to the procedure room and placed on a fluoroscopy table. The animal was connected to monitoring equipment including pulse oximetry, exhaled $CO_2$, and 12-lead ECG. The surgical site was scrubbed with chlorhexidine and betadine scrub (5 min each) and then sprayed with betadine solution. After sterile prep, the surgical site was draped with sterile sheets and towels.

Animals were not treated prophylactically for heart rate, blood pressure or arrhythmias. In defibrillator implantation procedures, animals were given 1 g cefazolin as prophylaxis against infection.

After sterile preparation, the right external jugular vein and right internal carotid artery were isolated by cut-down. The carotid arterial sheath was connected to a transducer to monitor blood pressure. A 2.7 Fr balloon catheter was inserted through a Judkins JL 3.5 guide catheter into the middle portion of the left anterior descending coronary artery (LAD) immediately distal to the second diagonal branch. Catheter position within the vessel was verified by infusion of iohexol radiographic contrast dye. The balloon was expanded to 4 atm, and the LAD was occluded for 150 minutes. During infarction, blood pressure was treated by dopamine infusion (2-20 mcg/kg/min), phenylephrine bolus (50-200 mcg) or epinephrine bolus (0.1-0.5 mg) and arrhythmias were treated with amiodarone infusion (150 mg over 10 min), as needed.

An implantable cardioverter-defibrillator (ICD, Boston Scientific, Natick, MA) was inserted into a subcutaneous pocket in the left neck and connected to a high voltage active-fixation lead placed through the external jugular vein into the right ventricular apex under fluoroscopic guidance. Lead pacing parameters (R wave>10 mV, pacing threshold<1 V, impedance 300-800Ω) were evaluated using a pace-sense analyzer (Medtronic, Mounds View, MN). ICD programming included only VVI pacing at 40 beats per minute, arrhythmia detection was turned off. The ICD was used for programmed stimulation and, if necessary, defibrillation during electrophysiology study. Back-up pacing was activated but not used in any animal.

After completion of the balloon occlusion, catheters and sheaths were removed, and hemostasis was achieved by ligation of the vessel. If pressors were still infusing, they were weaned prior to removal of the arterial sheath. In the post-operative period, the animals were treated with narcotics and non-steroidal anti-inflammatory drugs for pain management. Daily care consisted of observation for overall well-being, pain control, and gross assessment of input, output and respiration.

Electrophysiology Study (EPS):

For all studies, ECG and intracardiac electrograms were recorded using the EP-Workmate system (EP MedSystems, St. Jude Medical, West Berlin, NJ).

Non-Invasive EPS:

On a weekly basis, animals underwent programmed stimulation of the ventricles to assess VT inducibility. Non-invasive EPS was performed using the ICD. Prior to non-invasive EPS, animals were sedated with ketamine/xylazine/telazol (3 mg/kg of each). Before starting the arrhythmia induction protocol, electrogram amplitude, pacing threshold, pacing and shock electrode impedance measurements were measured through the defibrillator using the company-specific programmer. The arrhythmia induction protocol was performed using the programmed stimulation protocol described below. If VT was induced, 10 seconds of 12-lead ECG recording were obtained with the EP system and then the animal was paced out of the rhythm using the ICD antitachycardia pacing algorithms. If burst pacing failed, the animal was shocked internally from the ICD. If VF was induced, the animal was immediately shocked through the ICD, and if needed from an external defibrillator. Since the ICD lead was fixed in the RV apex, only single site programmed stimulation was performed during the non-invasive EPS.

Invasive EP Study:

Invasive EPS was performed immediately prior to sacrifice, 5 weeks after infarction. For all EPS measurements, isoflurane was used at a fixed dose of 1.75%.

In the initial 5 VT mapping/molecular analysis animals, the left carotid artery and external jugular vein were isolated by cut-down and a sheath was placed in each vessel. The chest was opened by median sternotomy. Sinus rhythm voltage mapping, VT induction and VT 3-dimensional mapping were performed using protocols described below. At the completion of mapping, all data were reviewed to verify that activation and entrainment criteria had been met and the marked VT site was snap frozen with liquid nitrogen-cooled forceps, cut free of the remaining heart tissue, freed from the forceps, immersed in RNAlater (Qiagen, Waltham MA) and stored initially in liquid nitrogen and later in a −80° C. freezer until used for mRNA measurements.

In the subsequent 10 functional assessment animals, the chest was opened by median sternotomy. The pericardial sac was incised to expose the heart. The left carotid artery and external jugular vein were isolated by cut-down and a sheath was placed in each vessel. Monophasic action potential (MAP) and bipolar electrogram recordings were obtained at 1 cm intervals around and through the MI scar border. Border zone location was established by direct visualization and confirmed by observation of decrease in electrogram voltage from adjacent sites. MAP recordings were obtained by placing a multipolar electrophysiology catheter perpendicular to the tissue and applying pressure. Monophasic electrograms are recorded with the electrode 3(−) to electrode 1(+). MAP recordings were obtained during fixed rate pacing from catheter poles 2 and 4 for 8 beats at 400 with abrupt switch to 250 ms for an additional 8 beats. At each MAP site, bipolar electrograms were recorded during sinus rhythm. Both MAP and bipolar electrogram recordings were low pass filtered at 500 Hz, and bipolar recordings were additionally high pass filtered at 30 Hz, as per convention. After completion of electrogram recordings, programmed stimulation was performed using the protocol described below. If VT was induced, mapping was performed as described below. After completion of the mapping procedure, 10,000 units of heparin was administered intravenously and then the heart was harvested. The coronary arteries were flushed with cardioplegic solution and the heart was stored in ice-cold cardioplegic solution for the 3-5 minutes required for transport to the optical mapping room.

Programmed Stimulation to Induce VT:

For arrhythmia induction, the following protocol was performed from the ICD lead in non-invasive studies, and initially from a quadripolar catheter placed in either the right (molecular analysis animals) or left (MAP recording animals) ventricular apex for invasive studies. In the invasive studies, after completion of ventricular apical pacing, the catheter was repositioned to the right ventricular outflow track (molecular analysis animals) or left ventricular lateral wall (MAP animals) and the arrhythmia induction protocol was performed at that site. The same stimulation protocol was used in the optical mapping experiments to induce VT in myocardial tissue wedges. All pacing was performed at twice the pacing threshold.

Extra-stimuli were delivered after eight ventricular drive beats (pacing cycle length 250, 300, and 350 ms). The first extra stimulus (S2) was initially set 200-240 ms after the last pacing stimulus of the drive train (S1). S2 was then delivered at progressively shorter coupling intervals, scanning in 10 ms steps until the effective refractory period (ERP) was reached. If no arrhythmias were observed, S2 was reset to a point 30 ms outside the ERP. A second extra stimulus (S3) was then added 170-200 ms after S2 and scanning in 10 ms decrements was repeated until S2 and S3 were both refractory or equal to 140 ms. Again, if no arrhythmias were induced, a third extra stimulus (S4) was similarly introduced and scanning in 10 ms decrements was repeated until S2-4 were refractory or a minimum coupling interval of 140 ms was reached. If VF was induced, the animal was immediately defibrillated from the ICD and from an external defibrillator if ICD shock failed to restore sinus rhythm. If VT was induced, 12-lead ECG recording was obtained and compared to prior VT inductions. The number of different 12-lead ECG morphologies of VT was tracked for each animal. VT mapping was performed as described below.

3-D Mapping Procedure:

For the initial 5 animals where the VT circuit was identified and then harvested for molecular analysis. The cardiac pathways RPM mapping system was used for 3-dimensional localization of the VT circuit (Boston Scientific, Natick, MA). Catheters were placed in the right ventricular apex and coronary sinus from the jugular venous sheath and in the left ventricle from the carotid sheath. Voltage mapping during sinus rhythm was performed to identify border zone and dense scar areas by movement of the catheter around the left ventricle and recording the voltage at each position. A minimum of 50 points were collected per animal, with the majority of points focused in the area within and around the infarct scar. After completion of the sinus rhythm map, VT was induced by programmed stimulation. All animals had hemodynamically unstable VT, so mapping consisted of repeated cycles of: VT induction, verification of identical 12-lead morphology for the induced VT, collection of approximately 10 mapping points over 30-60 seconds, cardioversion and then recovery for 3-5 minutes, until sufficient detail was obtained to visualize VT circuit activation. A minimum of 100 activation points was obtained for each VT circuit map.

After completion of the activation map, concealed entrainment criteria were assessed at map locations where mid-diastolic activation was observed. The mapping catheter was placed at these points, pacing threshold was measured, VT was induced, pacing stimuli were delivered at a rate 10-20 ms faster than the VT cycle length and stimulus strength twice threshold. If pacing failed to capture the ventricles, pacing rate and/or output strength were adjusted to achieve capture. After entrainment pacing, the VT was terminated by either burst pacing or shock. The 12-lead ECG morphology during pacing was compared to the VT morphology and the timing of the first post-pacing beat (by convention, called the post-pacing interval—PPI) was compared to the VT cycle length. The VT circuit protected isthmus was considered to be the area that had a PPI within 20 ms of the VT cycle length, an identical 12-lead ECG morphology of entrainment pacing and VT, and mid-diastolic activation. The catheter position at the successful entrainment site was marked with India ink dye injection. At the conclusion of the study, a transmural tissue section at the marked VT location was snap frozen and harvested using a liquid nitrogen-cooled 0.25" cork borer.

For the 10 functional assessment animals and the 5 validation cohort animals, VT site was identified by a combination of endocardial and epicardial activation mapping, performed using an endocardial 64-polar multielectrode basket catheter in the left ventricular endocardium and a decapolar electrophysiology catheter in the left and right ventricular epicardium. Epicardial catheter location was tracked by visualization and endocardial catheter position was determined by comparison to epicardial position marking under fluoroscopy. VT was induced using the programmed stimulation protocol described above. During VT, endocardial electrograms were recorded from the basket catheter and epicardial electrograms were recorded sequentially from 6-10 pre-determined epicardial catheter positions equally spaced along the ventricular epicardium. VT was terminated by burst pacing or cardioversion and the site of earliest electrical activation and the progression of activation were noted on the EP recordings. Concealed entrainment was assessed as described above. The schematic in FIG. 1 depicts this manual mapping method.

Quantitative Polymerase Chain Reaction:

Total RNA was extracted by RNeasy-Mini Kit (Qiagen), and reverse transcription used the Superscript First strand Synthesis system (Invitrogen). After reverse transcription, the amount of cDNA was adjusted to 10 ng, and real-time PCR was performed using SYBR green with the ABIprism 7900HT (Applied BioSystems) and primers designed using PrimerExpress (Applied BioSystems). Transcripts were normalized to 18S ribosomal RNA. Primers are as follows:

| gene | direction | primer | SEQ ID NO |
|---|---|---|---|
| KCNQ1 | sense | CGTGCGATTCCCCAGAAGAG | 1 |
|  | antisense | AGTCTCCCCTTCCAGGTCCA | 2 |
| KCNH2 | sense | CTGCTGAAGGAGACGGAGGA | 3 |
|  | antisense | TGGCGTTGACGTAGGTGGTG | 4 |
| KCNE1 | sense | ATGGCCCTGTCCAATTCCAC | 5 |
|  | antisense | AGCCTCCAGCTTGCTGTCAT | 6 |

-continued

| gene | direction | primer | SEQ ID NO |
|---|---|---|---|
| KCNE2 | sense | GATGCGGAGAACTTCTACTACGTCA | 7 |
|  | antisense | TCCTCCACGATGTACTGGTGG | 8 |
| KCNE3 | sense | TGCTATGGAGACTACCAATGGGACCGAG | 9 |
|  | antisense | CCGCCGCTCCTCAGTCAGGTG | 10 |
| KCNE4 | sense | TCCTTCTACGGCATTTTCTTGA | 11 |
|  | antisense | CATGGGCAGCGGCTTCATAG | 12 |
| KCNJ2 | sense | GGACCTTACTCTTCCCGTTC | 13 |
|  | antisense | GTGTGAGAACCAACCGCTAC | 14 |
| CACNA1C | sense | GTGTTCCAGTGCATCACCATGG | 15 |
|  | antisense | GTTGACAGATTCGGTCTCACTTG | 16 |
| SCN5A | sense | GTCTTCTGCCTCAGCGTCTT | 17 |
|  | antisense | TACGATTGAGCACCGTCAAG | 18 |
| GJA1 | sense | AGGTGGACTGTTTCCTCTCTCG | 19 |
|  | antisense | CGATCCTTAACACCCTTGAAGAAGAC | 20 |
| 18S ribosomal RNA loading control: | | | |
|  | sense | GTTGTTGCCATGGTAATCCTGCTCAGTACG | 21 |
|  | antisense | TCTGACTTAGAGGCGTTCAGTCATAATCCC | 22 |

Optical Mapping:

The cardiac ventricles were removed from the remaining heart and dissected into LV free wall, septum and RV free wall sections by cutting along the right and left septal borders. In the LV free wall section, the branches of the left anterior descending and circumflex coronary arteries that were perfusing infarct scar or border zone territory were identified. Starting with the branch perfusing the basal anterior-septal region (generally the second diagonal branch of the LAD), each branch noted to perfuse a section of infarct scar or border zone was cannulated and the perfusion territory was dissected free of the remaining LV free wall into an individual myocardial tissue wedge. The LAD was opened and branches perfusing the septal border zone were identified, cannulated and dissected into myocardial wedges similar to the LV free wall. The RV was not used. An LV free wall wedge from a region identified in VT mapping to be a VT circuit was used for cell isolation and patch clamp as described below. The remaining tissue wedges were used for optical mapping experiments. Optical mapping tissue wedges were perfused with cardioplegia and stored in ice cold cardioplegia solution until use.

To perform optical mapping of electrical activity, an individual myocardial tissue wedge was perfused with oxygenated Tyrode's solution at a perfusion pressure of 50-60 mmHg. Poorly perfused edges of the tissue were trimmed, and open vessel ends were ligated prior to use. The tissue was immersed in 37° C. perfusate and stabilized against a flat imaging window within a plexiglass chamber. The preparation was perfused with the voltage-sensitive dye di-4-ANEPPS (15 µM) for 10 min and then the excitation-contraction uncoupler, blebbistatin (10 µM) for 10-20 minutes (until contraction ceased). For recordings, the dye was excited with a tungsten-halogen light source (Oriel Instruments, Stratford, CT) through a 514±5 nm bandpass filter. The fluoresced light was high-pass filtered at 610 nm and recorded onto a 16×16-element photodiode array (model C4675; Hamamatsu) through high numerical aperture photographic lenses using a tandem-lens configuration (Nikon; 85 mm, F/1.4 and 105 mm, F/2.0). The optical signals were amplified with a variable gain (1×, 50×, 200×, 1000×), filtered with a variable cutoff low-pass filter, AC coupled with a variable time constant (1.8 sec, 2.2 sec, 10 sec, DC). Membrane potentials were recorded with sufficient voltage (1 mV), temporal (0.3 ms) and spatial (0.9 mm) resolution to monitor the time course of the AP simultaneously from 256 sites in a 4.5×4.5 mm area (giving 350 µm resolution between recording sites). Recordings of the myocardial wedge surfaces were made during constant rate pacing at 1000 ms cycle length. After constant rate pacing, programmed stimulation was performed using the protocol described above to induce VT. If VT was induced, a recording was made of each wedge surface.

Recorded signals were processed with custom software to mark activation (50% of peak) and repolarization (90% from peak back to baseline) time points for each pixel. Conduction velocities were calculated from the tissue activation data. APD90 was calculated from activation and repolarization data. VT circuits (if visible) were identified from analysis of the activation pattern during VT.

Cell Isolation and Patch Clamp:

Ventricular myocytes were isolated from sections of myocardium using the following protocol: A wedge of border zone tissue was perfused with Krebs' buffer for 5 minutes at 30-40 ml/min, at which time any unperfused segments are removed and open vessels were ligated. The wedge was next perfused with nominally calcium-free solution of the following composition (in mM): 130, NaCl; 5.4, KCl; 2 MgSO4; 0.5 NaH2PO4; 10, glucose; 5, HEPES; 20, Taurine; pH 7.2-7.4 with 100% O2; 37° C. for 2.5 minutes. Perfusion was then switched to digesting solution into which 0.05 mM $Ca^{2+}$, 1.5 mg/ml collagenase (Type II, Worthington), 0.1 mg/ml protease (fraction XIV, Sigma) were added. This solution was then recirculated for approximately 55 min at 10 ml/min. After digestion, the tissue was minced with HK Solution of the following composition (in mM): 110, L-Glutamic acid Monopotassium salt; 25, KCl; 3.5 MgCl2; 10, KH2PO4; 20, glucose; 5, HEPES; 20, Taurine; 0.5, EGTA; 5, Creatine; pH 7.2 and filtered into culture tube through a 200 µm nylon mesh filter. Two hours later myocytes were centrifuged and stored with Medium 199 and kept at room temperature until use.

For analysis, only rod-shaped cells with clear striations and no visible blebs were used. Isolated myocytes were placed in the Tyrode's solution composed of (mmol/L) NaCl 137, KCl 5.4, CaCl2 2.0, MgSO4 1.0, Glucose 10, HEPES 10, pH to 7.35 with NaOH. Microelectrodes were fabricated from TW150F borosilicate glass capillaries and filled with a solution of (mmol/L) aspartic acid 120, KCl 20, MgCl2 2, and HEPES 5, NaCl 10, EGTA 5, Na-GTP 0.3, Phosphocreatine 14, K-ATP 4, Creatine phosphokinase 2 and brought to a pH of 7.3. Action potentials and currents were recorded by ruptured-patch technique at 35° C. Cell capacitance and series resistance were compensated electronically at ~80%. Command and data acquisition were operated with an Axopatch 200B patch clamp amplifier controlled by a personal computer using a Digidata 1200 acquisition board driven by pCLAMP 7.0 software (Axon Instruments, Foster City, CA).

Action potentials were recorded under current clamp conditions. Myocytes were paced in the current clamp mode using a 1.5-2× diastolic threshold 5 ms current pulse at 1 Hz.

$I_{Ks}$ currents were elicited under voltage clamp conditions from a holding potential of −40 mV with depolarizing voltage pulses from −30 mV to 60 mV for 2.5 s and then return to −40 mV to generate outward tail currents in the presence of 5 µM E4031 to block $I_{Kr}$. The amplitude of tail currents was normalized to cell capacitance to obtain $I_{Ks}$ current density. The $I_{Ks}$ instantaneous component was calculated as the ratio of initial to peak current.

Measurements of $I_{Kr}$ currents were performed in the presence of 1 µM nisoldipine to block L-type Ca currents. $I_{Kr}$ currents were elicited from a holding potential of −40 mV with depolarizing voltage pulses from −30 mV to 60 mV for 750 ms and were isolated as E4031-sensitive tail current component upon return to −40 mV. The amplitude of E4031-sensitive tail currents was normalized to cell capacitance to obtain $I_{Kr}$ current density.

$I_{K1}$ currents were elicited from a holding potential of −40 mV with depolarizing voltage pulses from −100 mV to 40 mV for 150 ms, with 1 µM nisoldipine to block L-type Ca2+ currents. Peak current amplitude was normalized to cell capacitance to obtain $I_{K1}$ current density.

What is claimed is:

1. A method of identifying and correcting ventricular tachycardia (VT) circuits in the heart of a subject, the method comprising:
   (i) measuring a first action potential duration (APD) of a first tract of myocardial tissue of the subject;
   (ii) measuring a second action potential duration (APD) of a second tract of the myocardial tissue that is adjacent to the first tract;
   (iii) comparing the length of the first APD to the second APD;
   (iv) identifying a VT circuit in the heart of the subject when the first APD in the first tract is different from the second APD in the second tract; and
   (v) correcting the identified VT circuit by administering, to the subject, a composition that inhibits expression of KCNE3, a composition that inhibits expression of KCNE4, or a combination thereof.

2. The method of claim 1, wherein the first tract and/or the second tract are located completely or partially within a myocardial infarct scar of the heart.

3. The method of claim 1, wherein the measuring of the first APD and/or the measuring of the second APD is performed by unipolar electrogram, bipolar electrogram, monophasic action potential (MAP) recording, or optical mapping.

4. The method of claim 1, wherein the measuring comprises non-invasive mapping of unipolar activation-recovery intervals during sinus rhythm or fixed rate pacing of the subject's heart.

5. The method of claim 1, wherein the composition comprises:
   (a) an inhibitory nucleic acid; or
   (b) an isolated nucleic acid encoding a dominant-negative variant of KCNE3 protein.

6. The method of claim 5, wherein the inhibitory nucleic acid comprises any one of the sequences as provided in Table 1.

7. The method of claim 5, wherein the dominant-negative variant is KCNE3-V68T or KCNE3-V72T.

8. The method of claim 1, further comprising the step of ablating the cells of the VT circuit.

\* \* \* \* \*

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
cgtgcgattc cccagaagag        20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
agtctcccct tccaggtcca        20

<210> SEQ ID NO 3

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
ctgctgaagg agacggagga                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
tggcgttgac gtaggtggtg                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
atggccctgt ccaattccac                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
agcctccagc ttgctgtcat                                            20

<210> SEQ ID NO 7
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 7
gatgcggaga acttctacta cgtcatc                                    27

<210> SEQ ID NO 8
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 8
tcctccacga tgtactggtg g                                          21

<210> SEQ ID NO 9
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 9
```

```
tgctatggag actaccaatg ggaccgag                                        28

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 10
ccgccgctcc tcagtcaggt g                                               21

<210> SEQ ID NO 11
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 11
tccttctacg gcattttctt ga                                              22

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
catgggcagc ggcttcatag                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
ggaccttact cttcccgttc                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
gtgtgagaac caaccgctac                                                 20

<210> SEQ ID NO 15
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 15
gtgttccagt gcatcaccat gg                                              22

<210> SEQ ID NO 16
<211> LENGTH: 23
<212> TYPE: DNA
```

```
<213> ORGANISM: Artificial Sequence
<220> FEATURE:
<223> OTHER INFORMATION: Synthetic Polynucleotide

<400> SEQUENCE: 16
gttgacagat tcggtctcac ttg                                           23

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
gtcttctgcc tcagcgtctt                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
tacgattgag caccgtcaag                                               20

<210> SEQ ID NO 19
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 19
aggtggactg tttcctctct cg                                            22

<210> SEQ ID NO 20
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 20
cgatccttaa caccttgaa gaagac                                         26

<210> SEQ ID NO 21
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 21
gttgttgcca tggtaatcct gctcagtacg                                    30

<210> SEQ ID NO 22
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 22
tctgacttag aggcgttcag tcataatccc                                    30
```

<210> SEQ ID NO 23
<211> LENGTH: 103
<212> TYPE: PRT
<213> ORGANISM: Homo sapiens

<400> SEQUENCE: 23

Met Glu Thr Thr Asn Gly Thr Glu Thr Trp Tyr Glu Ser Leu His Ala
1               5                   10                  15

Val Leu Lys Ala Leu Asn Ala Thr Leu His Ser Asn Leu Leu Cys Arg
            20                  25                  30

Pro Gly Pro Gly Leu Gly Pro Asp Asn Gln Thr Glu Glu Arg Arg Ala
        35                  40                  45

Ser Leu Pro Gly Arg Asp Asp Asn Ser Tyr Met Tyr Ile Leu Phe Val
    50                  55                  60

Met Phe Leu Phe Ala Val Thr Val Gly Ser Leu Ile Leu Gly Tyr Thr
65                  70                  75                  80

Arg Ser Arg Lys Val Asp Lys Arg Ser Asp Pro Tyr His Val Tyr Ile
                85                  90                  95

Lys Asn Arg Val Ser Met Ile
            100

<210> SEQ ID NO 24
<211> LENGTH: 221
<212> TYPE: PRT
<213> ORGANISM: Homo sapiens

<400> SEQUENCE: 24

Met His Phe Leu Thr Ile Tyr Pro Asn Cys Ser Ser Gly Val Val Arg
1               5                   10                  15

Ala Gln Ser Arg Thr Glu Gln Lys Asn Pro Leu Gly Leu Asp Asp Leu
            20                  25                  30

Gly Ile Gln Asn Leu Gly Gln Thr Val Ser Leu Ala Pro Ala Val Glu
        35                  40                  45

Ala Ala Ser Met Leu Lys Met Glu Pro Leu Asn Ser Thr His Pro Gly
    50                  55                  60

Thr Ala Ala Ser Ser Ser Pro Leu Glu Ser Arg Ala Ala Gly Gly Gly
65                  70                  75                  80

Ser Gly Asn Gly Asn Glu Tyr Phe Tyr Ile Leu Val Val Met Ser Phe
                85                  90                  95

Tyr Gly Ile Phe Leu Ile Gly Ile Met Leu Gly Tyr Met Lys Ser Lys
            100                 105                 110

Arg Arg Glu Lys Lys Ser Ser Leu Leu Leu Tyr Lys Asp Glu Glu
            115                 120                 125

Arg Leu Trp Gly Glu Ala Met Lys Pro Leu Pro Val Val Ser Gly Leu
        130                 135                 140

Arg Ser Val Gln Val Pro Leu Met Leu Asn Met Leu Gln Glu Ser Val
145                 150                 155                 160

Ala Pro Ala Leu Ser Cys Thr Leu Cys Ser Met Glu Gly Asp Ser Val
                165                 170                 175

Ser Ser Glu Ser Ser Pro Asp Val His Leu Thr Ile Gln Glu Glu
            180                 185                 190

Gly Ala Asp Asp Glu Leu Glu Glu Thr Ser Glu Thr Pro Leu Asn Glu
        195                 200                 205

Ser Ser Glu Gly Ser Ser Glu Asn Ile His Gln Asn Ser
    210                 215                 220

<210> SEQ ID NO 25
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 25
ctgaacatgc tgcaggagag cgtggcgcc                                29

<210> SEQ ID NO 26
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 26
atggcaacga gtacttctac attctggtt                                29

<210> SEQ ID NO 27
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 27
ccggacgtgc acctcaccat tcaggagga                                29

<210> SEQ ID NO 28
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 28
gcagacgagg agctggagga gacctcgga                                29

<210> SEQ ID NO 29
<211> LENGTH: 99
<212> TYPE: PRT
<213> ORGANISM: Sus scrofa

<400> SEQUENCE: 29

Met Glu Thr Thr Asn Gly Thr Glu Thr Trp Tyr Glu Ser Leu His Ala
1               5                   10                  15

Val Leu Lys Ala Leu Asn Ala Thr Leu His Ser Asn Leu Leu Cys Arg
            20                  25                  30

Pro Gly Pro Asp His Leu Thr Glu Glu Arg Arg Ala Gly Leu Pro Gly
        35                  40                  45

Arg Asp Asp Asn Ser Tyr Met Tyr Ile Leu Phe Val Met Phe Leu Phe
    50                  55                  60

Ala Ala Thr Thr Gly Ser Leu Ile Leu Gly Tyr Thr Arg Ser Arg Lys
65                  70                  75                  80

Val Asp Lys Arg Ser Asp Pro Tyr His Val Tyr Ile Lys Asn Arg Val
                85                  90                  95

Ser Met Ile

<210> SEQ ID NO 30

```
<211> LENGTH: 297
<212> TYPE: DNA
<213> ORGANISM: Sus scrofa

<400> SEQUENCE: 30
atggaaacca ccaacggcac cgaaacctgg tatgaaagcc tgcatgcggt gctgaaagcg      60
ctgaacgcga ccctgcatag caacctgctg tgccgcccgg gcccggatca tctgaccgaa     120
gaacgccgcg cgggcctgcc gggccgcgat gataacagct atatgtatat tctgtttgtg     180
atgtttctgt ttgcggcgac caccggcagc ctgattctgg gctatacccg cagccgcaaa     240
gtggataaac gcagcgatcc gtatcatgtg tatattaaaa accgcgtgag catgatt       297

<210> SEQ ID NO 31
<211> LENGTH: 103
<212> TYPE: PRT
<213> ORGANISM: Homo sapiens

<400> SEQUENCE: 31

Met Glu Thr Thr Asn Gly Thr Glu Thr Trp Tyr Glu Ser Leu His Ala
1               5                   10                  15

Val Leu Lys Ala Leu Asn Ala Thr Leu His Ser Asn Leu Leu Cys Arg
            20                  25                  30

Pro Gly Pro Gly Leu Gly Pro Asp Asn Gln Thr Glu Glu Arg Arg Ala
        35                  40                  45

Ser Leu Pro Gly Arg Asp Asp Asn Ser Tyr Met Tyr Ile Leu Phe Val
    50                  55                  60

Met Phe Leu Phe Ala Val Thr Thr Gly Ser Leu Ile Leu Gly Tyr Thr
65                  70                  75                  80

Arg Ser Arg Lys Val Asp Lys Arg Ser Asp Pro Tyr His Val Tyr Ile
                85                  90                  95

Lys Asn Arg Val Ser Met Ile
            100

<210> SEQ ID NO 32
<211> LENGTH: 309
<212> TYPE: DNA
<213> ORGANISM: Homo sapiens

<400> SEQUENCE: 32
atggaaacca ccaacggcac cgaaacctgg tatgaaagcc tgcatgcggt gctgaaagcg      60
ctgaacgcga ccctgcatag caacctgctg tgccgcccgg gcccgggcct gggcccggat     120
aaccagaccg aagaacgccg cgcgagcctg ccgggccgcg atgataacag ctatatgtat     180
attctgtttg tgatgtttct gtttgcggtg accaccggca gcctgattct gggctatacc     240
cgcagccgca aagtggataa acgcagcgat ccgtatcatg tgtatattaa aaaccgcgtg     300
agcatgatt                                                           309
```